United States Patent [19]
Popescu et al.

[11] Patent Number: 6,090,406
[45] Date of Patent: Jul. 18, 2000

[54] POTENTIATION OF IMMUNE RESPONSES WITH LIPOSOMAL ADJUVANTS

[75] Inventors: Mircea C. Popescu, Plainsboro; Alan L. Weiner, Lawrenceville; Marie S. Recine, Hamilton Township, all of N.J.; Andrew S. Janoff, Yardley, Pa.; Leonard Estis; Lynn D. Keyes, both of Upton, Mass.; Carl R. Alving, Bethesda, Md.

[73] Assignee: The Liposome Company, Inc., Princeton, N.J.

[21] Appl. No.: 07/485,388

[22] Filed: Feb. 26, 1990

Related U.S. Application Data

[63] Continuation-in-part of application No. 07/425,727, Oct. 23, 1989, Pat. No. 5,231,112, which is a continuation-in-part of application No. 06/773,429, Sep. 10, 1985, Pat. No. 4,891,208, which is a continuation-in-part of application No. 06/721,630, Apr. 10, 1985, Pat. No. 4,721,612, which is a continuation-in-part of application No. 06/599,691, Apr. 12, 1984, abandoned, and a continuation-in-part of application No. 07/397,777, Aug. 23, 1989, abandoned, which is a continuation-in-part of application No. 07/277,854, Nov. 30, 1989, abandoned, and a continuation-in-part of application No. 07/236,701, Aug. 25, 1988, abandoned, and a continuation-in-part of application No. 07/236,702, Aug. 25, 1988, abandoned, and a continuation-in-part of application No. 07/277,854, Nov. 30, 1988, abandoned, and a continuation-in-part of application No. 07/128,974, Dec. 4, 1987, abandoned, and a continuation-in-part of application No. 07/061,186, Jun. 11, 1987, abandoned, which is a continuation-in-part of application No. 06/934,151, Nov. 24, 1986, abandoned, and a continuation-in-part of application No. 06/873,584, Jun. 12, 1986, abandoned, and a continuation-in-part of application No. 07/236,701, Aug. 25, 1988, abandoned, which is a continuation-in-part of application No. 07/128,974, Dec. 4, 1987, abandoned, and a continuation-in-part of application No. 07/236,702, Aug. 25, 1988, abandoned.

[51] Int. Cl.$^7$ .................. A61K 9/127; A61K 39/385; A61K 39/12; B01J 13/02
[52] U.S. Cl. .................. 424/450; 424/812; 424/196.11; 424/204.1; 424/206.1; 424/234.1; 264/4.1
[58] Field of Search .................. 424/196.11, 206.1, 424/204.1, 234.1, 265.1, 812, 88, 89, 92, 405; 264/4.1

[56] References Cited

U.S. PATENT DOCUMENTS

| | | | |
|---|---|---|---|
| 3,859,047 | 1/1975 | Klein | 23/230 |
| 4,053,585 | 10/1977 | Allison et al. | 424/92 |
| 4,117,113 | 9/1978 | Allison et al. | 424/89 |
| 4,201,767 | 5/1980 | Fullerton et al. | 424/89 |
| 4,396,630 | 8/1983 | Riedl et al. | 424/365 |

(List continued on next page.)

FOREIGN PATENT DOCUMENTS

| | | |
|---|---|---|
| 0 011 549 | 5/1980 | European Pat. Off. |
| 0 172 007 | 2/1986 | European Pat. Off. .......... A61K 9/50 |
| 0 177 223 | 4/1986 | European Pat. Off. .......... A61K 9/50 |
| 0 220 797 | 5/1987 | European Pat. Off. .......... A61K 9/50 |
| 0 240 346 | 10/1987 | European Pat. Off. .......... A61K 9/50 |
| 2 276 062 | 1/1976 | France . |
| 60-155109 | 8/1985 | Japan . |
| 61-24524 | 2/1986 | Japan . |
| WO85/04578 | 10/1985 | WIPO . |
| WO86/05977 | 10/1986 | WIPO . |
| 86/06959 | 12/1986 | WIPO .......... A61K 9/50 |
| WO87/04592 | 8/1987 | WIPO . |
| WO87/07506 | 12/1987 | WIPO . |
| 88/01864 | 3/1988 | WIPO .......... A61K 9/24 |
| 90/12595 | 11/1990 | WIPO .......... A61K 43/00 |

OTHER PUBLICATIONS

Harlow, Ed and David Lane, *Antibodies, A Laboratory Manual*, (Cold Spring Harbor Laboratory, Cold Spring Harbor, NY) pp. 96–97.

Almeida, et al., "Formation of Virosomes from Influenza Subunits and Liposomes", 1975, The Lancet, 899–901.

Alving, et al., "Preparation and Use of Liposomes in Immunological Studies", Chapter 11, Liposome Technology, vol. II, pp. 157–175, 1987.

Alving, C., "Liposomes as Carriers for Vaccines"; 1987; Liposomes: From Biophysics to Therapeutics, 195–218.

Alving, C. et al., "Effectiveness of Liposomes as Potential Carriers of Vaccines: Applications to Cholera Toxin and Human Malaria Sporozite Antigen"; 1986; Vaccine, 4:166–172.

Arrowsmith, et al., "The in vivo Release of Cortisone Esters from Liposomes and the Intramuscular Clearance of Liposomes", 1984, Int. J. Pharma. 20:347–362.

Davis, et al., "Liposomes as Adjuvants with Immunopurified Tetanus Toxoid: Influence of Liposomal Characteristics", 1987, Immunology 61:229–234.

Davis, D. et al., "Liposomes as Adjuvants with Immunopurified Tetanus Toxoid: the Immune Response", 1986/1987; Immunology Letters, 14:341–348.

(List continued on next page.)

*Primary Examiner*—Jose' G. Dees
*Assistant Examiner*—Michael G. Hartley
*Attorney, Agent, or Firm*—Kenneth B. Rubin; Rosanne Goodman

[57] ABSTRACT

A high integrity liposome comprising at least one stabile lipid and at least one peptide-like therapeutic agent associated with said liposome, adapted for parenteral administration to an animal, including a human, and method according to manufacture and use. Immunizing dosage forms comprising a liposome and an immunogen, wherein said liposome and immunogen are present in an immunization dose. Additionally, a dosage form, including such form particularly adapted to producing an immune response, comprising a salt according to an organic acid derivative of a sterol and an immunogen wherein said organic acid derivative of a sterol and immunogen are present in an immunization dose, and method according to use is disclosed. Further, a dosage form, including such form particularly adapted to producing an immune response, comprising dimyristoylphosphatidylcholine (DMPC)/cholesterol liposomes, optionally in an aluminum hydroxide gel, and an immunogen wherein said DMPC/cholesterol and immunogen are present in an immunization dose, and method according to use.

16 Claims, No Drawings

U.S. PATENT DOCUMENTS

| | | | |
|---|---|---|---|
| 4,416,872 | 11/1983 | Alving et al. | 424/177 |
| 4,522,803 | 6/1985 | Lenk et al. | 424/1.1 |
| 4,522,811 | 6/1985 | Eppstein et al. | 514/2 |
| 4,565,696 | 1/1986 | Heath et al. | 424/88 |
| 4,578,269 | 3/1986 | Morein | 424/88 |
| 4,588,578 | 5/1986 | Fountain et al. | 424/1.1 |
| 4,598,051 | 7/1986 | Papahadjopoulos et al. | 436/512 |
| 4,603,044 | 7/1986 | Geho et al. | 424/9 |
| 4,661,346 | 4/1987 | New et al. | 424/85 |
| 4,663,161 | 5/1987 | Mannino et al. | 424/89 |
| 4,721,612 | 1/1988 | Janoff et al. | 424/1.1 |
| 4,722,842 | 2/1988 | Stallcup et al. | 424/95 |
| 4,743,583 | 5/1988 | Speaker et al. | 514/4 |
| 4,745,074 | 5/1988 | Schreier et al. | 436/518 |
| 4,752,425 | 6/1988 | Martin et al. | 264/4.6 |
| 4,761,288 | 8/1988 | Mezei | 424/450 |
| 4,762,720 | 8/1988 | Jizomoto | 424/450 |
| 4,789,735 | 12/1988 | Frank et al. | 530/395 |
| 4,806,352 | 2/1989 | Cantrell | 424/92 |
| 4,826,687 | 5/1989 | Nerome et al. | 424/450 |
| 4,891,208 | 1/1990 | Janoff et al. | 424/450 |
| 5,013,555 | 5/1991 | Collins | 424/450 |
| 5,026,557 | 6/1991 | Estis et al. | 424/450 |
| 5,049,390 | 9/1991 | Wojdani | 424/450 |
| 5,100,662 | 3/1992 | Bolcsak et al. | 414/88 |

OTHER PUBLICATIONS

Eppstein, et al., "Controlled–Release and Localized Targeting of Inter–feron", 1986, Plenum Press, NY, Ed. Davis, et al., 277–283.

Gregoriadis, et al., "Liposomes as immunological adjuvants: antigen incorporation studies", 1987, Vaccine 5:145–151.

Jackson, et al., Intramuscular Absorption and Regional Lymphatic Uptaken of Liposome–Entrapped Inulin, 1981, Drug. Met. Dis. 9:535–540.

Kramp, et al., "Liposomal Enhancement of the Immunogenicity of Adenovirus Type 5 Hexon and Fiber Vaccines", 1979, Infec. and Immun. 25(2):771–773.

Latif, N. et al., "The Effect of Surface–coupled Antigen of Liposomes in Immunopotentiation"; 1987; Immunology Letters, 15:45–51.

North, J. et al., "Purified Epstein–Barr Virus $M_r$ 340,000 Glycoprotein Induces Potent Virus–neutralizing Antibodies when Incorporated in Liposomes"; 1982; Proc. Natl. Acad. Sci., 79:7504–7508.

Richards, R. et al., Liposomes, Lipid A, and Aluminum Hydroxide Enchance the Immune Response to a Synthetic Malaria Sporozoite Antigen; 1988; Infection and Immunity, 56:682–686.

Rooijen, N. et al., "Use of Liposomes as Biodegradable and Harmless Adjuvants"; 1983; Methods in Enzymology, 93:83–95.

Sanchez, Y. et al., Humoral and Cellular Immunity to Hepatitis B Virus–Derived Antigens: Comparative Activity of Freund Complete Adjuvant, Alum, and Liposomes; 1980; Infection and Immunity, 30:728–733.

POTENTIATION OF IMMUNE RESPONSES WITH LIPOSOMAL ADJUVANTS

This application is a continuation-in-part of Ser. No. 07/425,727, filed Oct. 23, 1989, now U.S. Pat. No. 5,231,112, which is a continuation-in-part of Ser. No. 06/773,429, filed Sep. 10, 1985, now U.S. Pat. No. 4,891,208, which is a continuation-in-part of Ser. No. 06/721,630, filed Apr. 10, 1985, now U.S. Pat. No. 4,721,612, which is a continuation-in-part of Ser. No. 06/599,691, filed Apr. 12, 1984, now abandoned. This application is also a continuation-in-part of Ser. No. 07/397,777, filed Aug. 23, 1989, now abandoned, which is a continuation-in-part Ser. No. 07/277,854, filed Nov. 30, 1988, now abandoned, and is a continuation-in-part of Ser. No. 07/236,701, filed Aug. 25, 1988, now abandoned, and is a continuation-in-part of Ser. No. 07/236,702, filed Aug. 25, 1988, now abandoned. This application is also a continuation-in-part of Ser. No. 07/277,854, filed Nov. 30, 1988, now abandoned, which is a continuation-in-part of Ser. No. 07/128,974, filed Dec. 4, 1987, now abandoned, and is a continuation-in-part of Ser. No. 07/061,186, filed Jun. 11, 1987, now abandoned, which is a continuation-in-part of Ser. No. 06/934,151, filed Nov. 24, 1986, now abandoned, and is a continuation-in-part of Ser. No. 06/873,584, filed Jun. 12, 1986, now abandoned. This application is also a continuation-in-part of Ser. No. 07/236,701, filed Aug. 25, 1988, now abandoned, which is a continuation-part of Ser. No. 07/128,974, filed Dec. 4, 1987, now abandoned, and is a continuation-in-part of Ser. No. 07/236,702, filed Aug. 25, 1988, now abandoned.

FIELD OF THE INVENTION

This invention relates to a number of liposomal dosage forms for therapeutic delivery of bioactive agents and for use in the vaccine arts.

In a first aspect, the present invention relates to a high integrity liposome comprising at least one stabile lipid and at least one peptide-like therapeutic agent (including an antigen or immunogen) associated with said liposome, adapted for parenteral administration to an animal, including a human. Also disclosed is a method of manufacture and use. Such liposomes are particularly useful for extended elaboration of peptide therapeutic agents as well as serving to protect said agents from degradation in the physiological environment. High integrity liposomes according to the present invention maintain their activity at the site of topical or parenteral administration, for example, after intramuscular, intraperitoneal, intraocular, intramammary or subcutaneous administration for periods often in excess of 24 hours. Therapeutic methods are also disclosed which utilize the extended elaboration of the liposomal dosage forms of the present invention to provide a treatment regimen which may be used to treat numerous conditions with a less invasive methodology than intravenous, intra-arterial or even daily injection.

Immunogenic dosage forms are also presented. These innumogenic dosage forms of the present invention exhibit surprising immunogenic activity.

In a second aspect of the present invention, certain stabile liposomes, e.g., DMPC/cholesterol liposomes are disclosed for use in the vaccine arts with a dosage form particularly adapted to producing an immune response, comprising DPMC/cholesterol liposomes, optionally in an aluminum hydroxide gel, and an immunogen wherein said DPMC/cholesterol liposomes and immunogen are present in an immunization dose, and method of use. Methods of using these dosage forms are also disclosed by the present invention.

In a third aspect of the present invention, an immunogenic dosage form is disclosed comprising a salt form of an organic acid derivative of a sterol and an immunogen wherein said organic acid derivative of a sterol and immunogen are present in an immunization dose. Also disclosed is a method of use related to these dosage forms. Methods of using these dosage forms are also disclosed.

BACKGROUND OF THE INVENTION

Peptide therapeutic agents are well known and are of increasing use in the pharmaceutical arts. Hormones, immunomodulators, and a host of newly discovered peptide and peptide-like compounds including certain immunogens are presently being administered to animals, including humans, in therapeutic regimens.

Consistent drawbacks to the parenteral administration of such peptide compounds have been the rapidity of breakdown or denaturation (loss of "native state configuration") of such compounds in the physiological environment and the difficulty of obtaining therapeutically effective dosage levels of such agents for extended periods. Infusion pumps, as well as wax or oil implants, have been employed in the therapeutic arts for chronic administration of therapeutic agents in an effort to both prolong the presence of peptide-like therapeutic agents and preserve the integrity of such agents. Furthermore, in particular cases in which the peptide-like therapeutic agent (which will be understood to include a protein or haptene) is to function as an immunogen, the peptide-like agent should (with particular reference to each epitope of the peptide-like agent) ideally maintain native state configuration for an extended period of time and additionally be presented in a fashion suitable for triggering an immunogenic response in the challenged animal.

One adaptation of the administration of peptide-like therapeutic agents is in the vaccine art. In this art immunogens are introduced into an organism in a manner so as to stimulate an immune response in the host organism. The induction of an immune response depends on many factors among which are believed to be the chemical composition and configuration of the immunogen, the immunogenic constitution of the challenged organism, and the manner and period of administration of the immunogen. An immune response has many facets, some of which are exhibited by the cells of the immune system, (e.g., B-lymphocytes, T-lymphocytes, macrophages, and plasma cells). Immune system cells may participate in the immune response through interaction with immunogen or other cells of the immune system, the release of cytokines and reactivity to those cytokines. Immune response is conveniently (but arbitrarily) divided into two main categories—humoral and cell-mediated. The humoral component of the immune response includes production of immunoglobulins specific for the immunogen. The cell-mediated component includes the generation of delayed-type hypersensitivity and cytotoxic effector cells against the immunogen.

In some instances the immune response is the result of an initial or priming dose of an immunogen that is followed by one or more booster exposures to the immunogen. Priming with relatively strong immunogens and liposomes is discussed in "Liposomal Enhancement of the Immunogenicity of Adenovirus Type 5 Hexon and Fiber Vaccines", Kramp, W. J. et al., Infection and Immunity, 25:771–773 (1979) and "Liposomes as Adjuvants with Immunopurified Tetanus Toxoid: the Immune Response", Davis, D. et al., Immunology Letters, 14:341–8 (1986/1987).

Ideally, an immunogen will exhibit two properties; the capacity to stimulate the formation of the corresponding antibodies and the propensity to react specifically with these antibodies. Immunogens bear one or more epitopes which are the smallest part of an immunogen recognizable by the combining site of an antibody.

In particular instances, immunogens, fractions of immunogens or conditions under which the immunogen is presented are inadequate to precipitate the desired immunological response. Insufficient immunity occurs as a result. This is often the case with peptides or other small molecules used as immunogens. Other substances such as immunomodulators (e.g., cytokines such as the interleukins) may be combined in vaccines as well.

The vaccine art recognizes the use of certain substances called adjuvants to potentiate an immune response when used in conjunction with an immunogen. Adjuvants are further used to elicit an immune response that is faster or greater than would be elicited without the use of the adjuvant. In addition, adjuvants may be used to create an immunological response using less immunogen than would be needed without the inclusion of adjuvant, to increase production of certain antibody subclasses that afford immunological protection or to enhance components of the immune response (e.g., humoral, cellular). Known adjuvants include Freund's Adjuvants (and other oil emulsions), Bordetella Pertussis, aluminum salts (and other metal salts), Mycobacterial products (including muramyl dipeptides), and liposomes.

As used herein, the term "adjuvant" will be understood to mean a substance or material administered together or in conjunction with an immunogen which increases the immune response to that immunogen. Adjuvants may be in a number of forms including emulsions (e.g., Freund's adjuvant), gels (aluminum hydroxide gel), particles (liposomes) or solid materials.

It is believed that adjuvant activity can be effected by a number of factors. Among such factors are (a) carrier effect, (b) depot formation, (c) altered lymphocyte recirculation, (d) stimulation of T-lymphocytes, (e) direct stimulation of B-lymphocytes and (f) stimulation of macrophages.

With many adjuvants, adverse reactions are seen. In certain cases, adverse reactions may include granuloma formation at the site of injection, severe inflammation at the site of injection, pyrogenicity, adjuvant induced arthritis or other autoimmune response, or oncogenic response. Such reactions have hampered the use of adjuvants such as Freund's adjuvant. The search continues for additional adjuvants that promote immunogenic activity yet are non-toxic to the host.

In particular embodiments of the present invention, liposomes are utilized as adjuvants either alone or in combination with other adjuvants. U.S. Pat. No. 4,053,585 issued Oct. 17, 1977 to Allison et al. states that liposomes of a particular charge are adjuvants. Immunogenic compositions according to the present invention are clearly distinguishable over this reference in both the composition and the magnitude of the immunogenic response associated with the composition. Other substances such as immunomodulators (e.g., cytokines such as the interleukins) may be combined in adjuvants as well. Davis, D, et al., "Liposomes as Adjuvants with Immunopurified Tetanus Toxoid: Influence of Liposomal Characteristics", Immunology, 61:229–234 (1987); and Gregoriadis, G. et al., "Liposomes as Immunological Adjuvants: Antigen Incorporation Studies", Vaccine, 5:145–151 (1987) report DMPC/cholesterol liposomes (in a weight ratio of 1:1) and immunogen as giving minimally improved (over free immunogen) immunological response in small unilamellar vesicles of a distinct dehydration/rehydration type with tetanus toxoid as the immunogen, a strong immunogen. In the Davis and in the Gregoriadis papers, the liposomal immunogenic response was only minimally distinguishable from the response of free immunogen. To distinguish the liposomal from free immunogen response, the authors found it necessary to dilute the tetanus toxoid to minimal response amounts. As distinguished from these references, the present invention adopts conditions of DMPC/cholesterol liposomes that yield therapeutically effective immunological response not taught by the prior art. The immunological responses produced by the dosage forms of the present invention are a surprising result. More importantly, the present invention teaches the use of DMPC/cholesterol liposomes as adjuvants for immunogenic agents that generally produce a weak immunogenic response or no immunogenic response.

Humoral immune response may be measured by many well known methods. Single Radial Immunodiffusion Assay (SRID), Enzyme Immunoassay (EIA) and Hemagglutination Inhibition Assay (HAI) are but a few of the commonly used assays of humoral immune response. SRID utilizes a layer of a gel such as agarose containing the immunogen being tested. A well is cut in the gel and the serum being tested is placed in the well. Diffusion of the antibody out into the gel leads to the formation of a precipitation ring whose area is proportional to the concentration of the antibody in the serum being tested. EIA, also known as ELISA (Enzyme Linked Immunoassay), is used to determine total antibodies in a sample. The immunogen is adsorbed to the surface of a microtiter plate. The test serum is exposed to the plate followed by an enzyme linked immunoglobulin, such as IgG. The enzyme activity adherent to the plate is quantified by any convenient means such as spectrophotometry and is proportional to the concentration of antibody directed against the immunogen present in the test sample. HAI utilizes the capability of an immunogen such as viral proteins to agglutinate chicken red blood cells (or the like). The assay detects neutralizing antibodies, i.e. those antibodies able to inhibit hemagglutination. Dilutions of the test serum are incubated with a standard concentration of immunogen, followed by the addition of the red blood cells. The presence of neutralizing antibodies will inhibit the agglutination of the red blood cells by the immunogen.

Tests to measure cellular immune response include determination of delayed-type hypersensitivity or measuring the proliferative response of lymphocytes to target immunogen.

Liposomes are completely closed lipid bilayer membranes containing an entrapped aqueous volume. Liposomes may be unilamellar vesicles (possessing a single bilayer membrane) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "head" orient towards the aqueous phase.

The original liposome preparation of Bangham, et al. (J. Mol. Biol., 1965, 13:238–252) involves suspending phospholipids in an organic solvent which is then evaporated to dryness leaving a phospholipid film on the reaction vessel. Next, an appropriate amount of aqueous phase is added, the mixture is allowed to "swell," and the resulting liposomes which consist of multilamellar vesicles (MLVs) are dispersed by mechanical means. This technique provides the basis for the development of the small sonicated unilamellar vesicles described by Papahadjopoulos et al. (Biochim. Biophys. Acta., 1968, 135:624–638), and large unilamellar vesicles. Small unilamellar vesicles have a diameter of about 100 nm or less.

Unilamellar vesicles may be produced using an extrusion apparatus by a method described in Cullis et al., PCT Application No. WO 87/00238, published Jan. 16, 1986, entitled "Extrusion Technique for Producing Unilamellar Vesicles" incorporated herein by reference. Vesicles made by this technique, called LUVETs, are extruded under pressure once or a number of times through a membrane filter.

A subclass of multilamellar vesicles are liposomes which are characterized as having substantially equal lamellar solute distribution. This class of liposomes is denominated as stable plurilamellar vesicles (SPLV) as defined in U.S. Pat. No. 4,522,803 to Lenk, et al., monophasic vesicles as described in U.S. Pat. No. 4,558,578 to Fountain, et al. and frozen and thawed multilamellar vesicles (FATMLV) wherein the vesicles are exposed to at least one freeze and thaw cycle; this procedure is described in Bally et al., PCT Publication No. 87/00043, Jan. 15, 1987, entitled "Multilamellar Liposomes Having Improved Trapping Efficiencies." U.S. Pat. No. 4,721,612 to Janoff et al. describes steroidal liposomes for a variety of uses. The teachings of these references as to preparation and use of liposomes are incorporated herein by reference.

OBJECTS OF THE PRESENT INVENTION

It is an object of the present invention to provide therapeutic dosage forms including peptide-like therapeutic agents in high integrity liposomes that may be administered via a topical or parenteral route.

It is an additional object of the present invention to provide liposomal therapeutic dosage forms which exhibit extended elaboration for periods of at least about 24 hours after topical or parenteral administration.

It is another object of the present to provide a therapeutic method for delivering peptide-like therapeutic agents for periods in excess of 24 hours.

It is a further object of the present invention to provide immunogenic dosage forms which exhibit enhanced immunogenic activity.

It is still an additional object of the present invention to provide a method for producing enhanced immunogenic responses using the immunogenic dosage forms of the present invention.

It is yet another object of the present invention to provide a specific method for efficiently producing an immunogenic reaction from an immunogen even where the immunogen produces no reaction or a weak reaction by itself.

These and other objects of the present invention may be readily determined from the detailed description of the invention which is set forth herein.

SUMMARY OF THE INVENTION

The present invention relates to a number of liposomal and immunogenic preparations. The present invention is presented in three parts.

In a first aspect, the present invention relates to a liposome, preferably a high integrity multilamellar liposome such as a stabile plurilamellar vesicle (SPLV), comprising at least one stabile lipid and at least one peptide-like therapeutic agent associated with the liposome, adapted for parenteral administration to an animal. These therapeutic dosage forms exhibit extended elaboration when administered via a parenteral route other than an intravenous or intra-arterial route. In certain embodiments the stabile lipid is hydrogenated phosphatidylcholine or distearoyl phosphatidylcholine. In particular embodiments the therapeutic agent comprises an antigen.

The stabile liposomes of this aspect of the present invention may further comprise liposomes containing a lipid diluent, such as cholesterol. In some embodiments containing cholesterol, the cholesterol is present in a lipid:cholesterol molar ratio of from about 4:1 to about 1:1 (molar weight basis). In one embodiment distearoyl phosphatidylcholine (DSPC) and cholesterol are used in about a 7:3 mole % ratio of phospholipid to cholesterol. It is clearly preferred that the therapeutic liposomes according to this aspect of the present invention are multilamellar vesicles, preferably SPLV's. Preferably, the liposomes in this aspect of the present invention should be at least about 1 micron in diameter.

The peptide-like therapeutic agent in the liposomes of this invention include a hormone, an immunomodulator, glycosylated carrier protein, or galactosylated carrier protein, with particular reference to the peptide-like therapeutic agent being galactose-albumin, or the hormone being a somatotropin or calcitonin including analogues or derivatives thereof and other agents including nonproteinaceous molecules, for example, amino acid containing molecules and additional agents. In embodiments wherein the therapeutic agent is an immunomodulator, a particularly preferred embodiment utilizes an interleukin, such as IL2. Peptide-like therapeutic agents also include antigens in this aspect of the present invention.

This first aspect of the present invention also includes a method of treating an animal by administering to the animal a therapeutically effective dosage form of peptide-like therapeutic agent encapsulated in stabile, high integrity liposomes. In certain preferred embodiments of this method, the parenteral administration is preferably intramuscular, subcutaneous, intradermic, intraperitoneal, intramammary and intraocular. Liposomal dosage forms of the present invention have been shown to deliver a peptide-like therapeutic agent from the site of parenteral administration over an extended period, preferably at least about 24 hours.

The method of treating animals also includes the peptide-like therapeutic agent being a hormone, an immunomodulator or glycosylated carrier protein, or galactosylated carrier protein, for example, the hormones bovine somatotropin or calcitonin or the immunomodulator IL2 (including analogues, and derivatives and pharmaceutically acceptable salts of the foregoing).

In certain embodiments of the method of treating animals the protein-like therapeutic agent is a growth promotant and the treated animal is a pig, a chicken, a salmon, a cow or a human. In one particular aspect, the present invention provides a method of increasing milk production in dairy animals by administering to the animals a therapeutically effective amount of somatotropin in stabile, high integrity liposomes. Preferably, these high integrity stability liposomes are administered via a parenteral, preferably, intramuscular or intramammary route. In one particular aspect, the dairy animal is a cow and the somatotropin is bovine somatotropin or analogues or derivatives thereof.

In another embodiment of this first aspect of the present invention a high integrity liposome comprising at least one stabile lipid and at least one peptide-like therapeutic agent associated with said liposome, adapted for topical administration to an animal is presented. Topical dosage forms according to the present invention may be used to topically deliver a therapeutic agent for an extended period, for example, at least about 24 hours.

The present invention also relates to a number of immunogenic dosage forms, especially including stabile liposomes of the first aspect of the present invention, as a vaccine dosage form. The present invention therefore includes an immunizing dosage form comprising a liposome and an immunogen wherein said liposome and immunogen are present in an immunization dose. The liposome preferably comprises a mixture of DMPC and cholesterol.

In this vaccine aspect of the present invention the liposomes are preferably multilamellar liposomes comprising DMPC/cholesterol and the immunogen is utilized in an immunization dose. In one embodiment the liposome of this dosage form comprises a molar ratio of about 80 to about 20 DMPC and about 20 to about 80 cholesterol. Preferably, the ratio of DMPC to cholesterol ranges from about 30:70 to about 70:30. Most preferably, the ratio of DMPC to cholesterol is 70:30. In other embodiments according to the present invention, the ratio of DMPC to cholesterol ranges from about 60:40 to about 40:60. Preferably, the immunogenic dosage form includes aluminum adjuvants such as aluminum hydroxide gel. In specific embodiments the dosage form is a multilamellar liposome, preferably an SPLV at least about 1 micron in diameter and most preferably a 70:30 DMPC/cholesterol SPLV having a diameter no less than about 1 micron.

In particular embodiments of this dosage form, the immunogen is selected from the group comprising proteins, peptides, polysaccharides, bacterial fractions, viral fractions, protozoal fractions, synthetic peptides or lipopolysaccharides. The dosage form may further comprise an immunomodulator including a cytokine. Preferred dosage forms of the DMPC/cholesterol immunogenic dosage forms include influenza immunogens, preferably the hemagglutinin or bromelain fragments.

In a third aspect of the present invention, an immunogenic dosage form comprising a liposome made from a salt form of an organic acid derivative of sterol in combination with an immunogenic amount of an immunogen is presented. In certain preferred embodiments of this aspect of the present invention, the immunogen is an influenza fragment, most preferably the hemagglutinin or bromelain fragment. In certain dosage forms the immunogen is entrapped in the liposome, preferably a multilamellar vesicle at least about 1 micron in diameter. A particularly useful liposome of this immunogenic aspect of the present invention comprises a tris (hydroxymethyl) aminomethane salt form of an organic acid derivative of a sterol. In certain preferred embodiments according to the present invention, the immunogen comprises an influenza immunogen, more particularly, the hemagglutinin fragment or the bromelain fragment of the influenza virus.

In certain preferred embodiments of the present invention the immunogenic dosage form includes the salt form made of an organic acid derivative of a sterol and tris (hydroxymethyl) aminomethane or other ions, for example sodium. In other embodiments the salt form is a carboxylic acid derivative of a sterol (such as an aliphatic carboxylic acid, particularly those up to five carbon atoms), a salt form of a dicarboxylic acid derivative of a sterol (such as an aliphatic dicarboxylic acid, particularly those up to seven carbon atoms), an hydroxy acid derivative of a sterol (such as citric acid), an amino acid derivative of a sterol or a salt form of a polyamino acid derivative of a sterol, or a salt form of a polycarboxylic acid derivative of a sterol. In one preferred embodiment of the dosage form, the aliphatic dicarboxylic acid is succinate.

In embodiments of the vaccine or immunogenic dosage form of this invention, the immunogen may be selected from the group comprising proteins, peptides, polysaccharides, nucleic acids, lipids, glycolipids, lipoproteins, lipopolysaccharides, synthetic peptides or bacterial fractions, viral fractions, protozoal fractions, tissue fractions, or cellular fractions. Specific immunogens are influenza fractions such as hemagglutinin and its components, parainfluenza antigens (fusion and hemagglutinin-neuraminidase), virus fractions, parasite components such as malaria sporozoite fractions, microbial fractions such as hemophilus, pertussis, gonococcus, hepatitis (A, B, and non-A/non-B) fractions, meningococcus fractions, HIV fractions (all strains), and cancer cell fractions such as melanoma fractions. The dosage form of this immunogenic aspect of the present invention may further include an immunomodulator such as a lympkokine or cytokine.

This invention also relates to a method of potentiating an immune response in an animal, including a human, comprising the step of administering to such animal an immunization dose of a composition comprising an immunogenic dosage form of the present invention such an organic acid derivative of a sterol or a liposome comprising DMPC and cholesterol and an immunogen. In one embodiment the method for potentiating the immune response includes a liposome, preferably a multilamellar vesicle at least about 1 micron in diameter. In some embodiments the immunogen is entrapped in the liposome. Methods of potentiating an immune response utilizing the previously described immunogenic dosage forms are also disclosed.

In an additional method of the present invention a method of potentiating an immune response in an animal is disclosed which comprises a first step of administering to the animal a priming immunization dose of a composition comprising a liposome adjuvant—any type of liposome—and particularly a liposome which comprises DMPC/cholesterol or an organic acid derivative of a sterol and an adjuvant-obligatory immunogen. In a second step, a booster dose of adjuvant-obligatory immunogen is administered to potentiate the priming dose. It has been surprisingly found that this method of priming with an adjuvant of the present invention in combination with an immunogen—even an immunogen which produces a weak response or even no response—will produce a substantial immune response when a booster dose of adjuvant obligatory immunogen in the absence of adjuvant is given.

In this two step method of priming, specific instances make use of a liposome such as a multilamellar vesicle made of an organic derivative of sterol. The SPLV liposome is preferably at least about 1 micron in diameter, and preferably comprises DMPC/cholesterol in a weight ratio of about 70:30. In further preferred embodiments of this aspect of the present invention the DMPC/cholesterol liposomes include aluminum adjuvants such as aluminum hydroxide gel. Specific immunogens of the DMPC/cholesterol liposomal dosage form and the methods of this aspect of the present invention are influenza fractions such as hemagglutinin and its components, parainfluenza antigens (fusion and hemagglutinin-neuraminidase), virus fractions, parasite components such as malaria sporozoite fractions, microbial fractions such as hemophilus, pertussis, gonococcus, hepatitis (A, B, and non-A/non-B) fractions, meningococcus fractions, HIV fractions (all strains), and cancer cell fractions such as melanoma fractions. The dosage form of this immunogenic aspect of the present invention may further include an immunomodulator such as a lymphokine or cytokine.

Alternatively, this step-wise method of priming an immune response in an animal, in one particular embodiment, utilizes a salt form of an organic acid derivative of a sterol wherein the salt form comprise a tris (hydroxymethyl) aminomethane or other ions such as sodium and an organic acid derivative of a sterol. In one particularly preferred aspect of this priming method, the use of an immunogen that would not generate an immune response absent an adjuvant is particularly included in this embodiment. This is a particularly surprising result because such a method may be used to develop immunity to a number of harmless, otherwise non-reactive immunogens.

In other embodiments of the method of priming an immune response any of the dosage forms as previously described may be used with particular reference to liposomes formed from salt forms of carboxylic acid derivatives of a sterol (such as an aliphatic carboxylic acid, particularly those up to five carbon atoms), salt forms of a dicarboxylic acid derivative of a sterol (such as an aliphatic dicarboxylic acid, particularly those up to seven carbon atoms), hydroxy acid derivatives of sterols (such as citric acid), amino acid derivatives of sterols or salt forms of a polyamino acid derivative of a sterol, or salt forms of a polycarboxylic acid derivative of a sterol.

In preferred versions of the step-wise priming method of the present invention which utilize a liposome formed from salt forms of sterols, or multilamellar liposomes, especially those of about 1 micron or more are used. Other liposomes may be used in this method, for example liposomes that comprise phosphatidylcholine, cholesterol, phosphatidyl serine or phosphatidyl ethanolamine. A preferred embodiment of the method of priming further includes immunizing a primed animal by the step of administering to said animal at least one booster dose of an adjuvant-obligatory immunogen absent adjuvant.

In addition to the above-described components, the liposomal dosage forms of the present invention may additionally comprise a suitable pharmaceutical carrier.

BRIEF DESCRIPTION OF THE TABLES

Table A, example 5, shows the substantial period during which IL-2 remains at the injection site in mice receiving 2.7 mg/kg in 10 mg of high integrity liposomes (ESPC/cholesterol).

Table B, example 5, shows the retention evidenced in Table A, was accompanied by a persistence of available bioactive interleukin.

Table C, example 6, shows the retention at the site of injection of galactose-albumin encapsulated in high integrity liposomes. As shown, radioactivity from galactose-albumin encapsulated in high integrity liposomes was evidenced 14 days after injection, whereas free radioactive material was eliminated in a single day.

Table D, example 6, shows that injected encapsulated material remaining at the site of injection retains bioactivity for an extended period compared to the retention of unencapsulated material.

Table 1A compares the antibody response in guinea pigs immunized with Influenza B/Ann Arbor hemagglutinin (HA) alone or entrapped within $CHS_{tris}$ liposomes. HA elicits a particular level of antibody response without adjuvant, but this response is enhanced by adjuvant. $CHS_{tris}$ liposomes are seen from the results to potentiate this antibody production. In particular, neutralizing antibody responses as detected by HAI to 5 or 0.5 ug of HA are increased up to about 50-fold and 70-fold respectively when HA is administered with the steroidal adjuvant, when HA is administered with a steroidal adjuvant such as $CHS_{tris}$.

Table 1B shows the antibody response in guinea pigs immunized with the bromelain fragment of HA (HAB) in various formulations. HAB is generally non-immunogenic when administered alone and is exemplary of an adjuvant-obligatory immunogen. Use of steroidal adjuvant in the form of CHS increases the immune response on a par or better than complete Freund's adjuvant, especially the production of protective neutralizing antibodies as detected by HAI. This increase may be about 1400-fold. Furthermore, increasing the amount of adjuvant increases the immune response.

Table 2 demonstrates the importance of priming in generation of the immune response. HAB is seen to generate a weak immune response that is not greatly potentiated on secondary challenge, even with adjuvant of this invention. However, when HAB is administered in association with the adjuvant of this invention, here in the form of a $CHS_{tris}$ liposome a substantial immune response is generated upon application of a second inoculation of HAB, here in solution. It is an important aspect of the present invention that priming of the subject animal with an immunogenic dose of adjuvant-obligatory immunogen and adjuvant permitted later booster doses to be highly effective wherein such booster doses did not contain adjuvant but merely contained adjuvant-obligatory immunogen. This is a particularly surprising result. The priming of immune response with the adjuvant of this invention permits booster administrations of adjuvant-obligatory immunogen without adjuvant, even when the immunogen would not have initially generated an immune response without coadministration with an adjuvant. In this embodiment of the invention it is important to note than any liposome can be used as a priming adjuvant, not just steroidal liposomes, for use with adjuvant-obligatory immunogens.

Table 3 discloses that superior results are obtained when the immunogen is entrapped in an adjuvant liposome of the present invention and not merely adsorbed with the adjuvant liposome. This is particularly true when the priming response is considered. Table 3 thus indicates that entrapment is a potentiator of priming response, even more than a potentiator of secondary response. Table 3 also shows that changing the salt composition from TRIS to sodium does not alter the adjuvant effect provided by CHS liposomes.

Table 4 compares the antibody response in guinea pigs immunized with the bromelain fragment of Influenza B/Ann Arbor hemagglutinin (HAB) in various forms. HAB is poorly immunogenic when administered alone or when administered with aluminum hydroxide gel. The immunogenicity is greatly increased when HAB is entrapped within DMPC/cholesterol SPLV's at various mole ratios and lipid concentrations. Total anti-HA IgG responses detected by EIA are increased up to 5000 fold and protective neutralizing antibodies detected by HAI are increased up to 35 fold at 6 weeks when HAB is administered in DMPC/cholesterol SPLV's at 30:70 and 70:30 mole ratios, respectively. Increasing the lipid concentration also increases the adjuvant effect as demonstrated with 50:50 mole ratio formulations.

Table 5 demonstrates the adjuvant effect of DMPC/cholesterol SPLV's (70:30 mole ratio) on Influenza B/Ann Arbor hemagglutinin (HA). HA administered in free form is a good immunogen at 5 ug dose but elicits low antibody titers when administered at 0.5 ug. Liposomal HA at both of these dosages generates responses which are up to 80 fold higher than free HA.

Table 6 demonstrates the adjuvant effect of DMPC/cholesterol SPLV's and aluminum hydroxide gel. As seen in Experiment I, administration of HAB, with DMPC/cholesterol liposomes (200 mg starting lipid concentration) generates a total anti-HA IgG response up to 100 fold greater and a neutralizing antibody titer 10 fold greater than HAB alone. Increasing the starting lipid concentration to 500 mg increases the adjuvant effect even more (500 fold and 30 fold respectively). When the same formulations are administered with aluminum hydroxide gel, even these high titers are increased up to 3 times greater. The combined adjuvant effect for liposomes and aluminum hydroxide is clearly evident in Experiment II. As in the first experiment, liposomal HAB increases antibody responses up to 200 fold over free HAB (5 ug dose). Administration with aluminum hydroxide gel substantially increases even these titers up to 5 times greater. Most striking is the observation that when a dose of 0.5 ug liposomal HAB is administered with aluminum hydroxide a response equivalent to 5 ug liposomal HAB is seen.

Table 7 set forth at the end of Example 32 of the present application compares the adjuvant effect of CHS containing sterol liposomes (containing 100% negatively charged lipids), DMPC/cholesterol liposomes and DMPC/cholesterol liposomes containing amounts of the negatively charged lipid, DMPG. The results showed that CHS containing liposomes and DMPC/cholesterol liposomes evidenced surprisingly high adjuvancy whereas the inclusion of a minor component of the negatively charged lipid DMPG actually decreased the adjuvancy effect of DMPC/cholesterol liposomes.

Table 8 shows the results obtained with HA used for vaccination after splitting the influenza virus with detergent. The results of Table 8 show that 5 ug of antigen in $CHS_{tris}$ liposomes induced a strong adjuvant effect regardless whether this amount of antigen was entrapped in 13.6 or 1.9 mg of lipid. The same observation can be made in the case of DMPC/chol formulations.

Furthermore, 1:10 dilution of $CHS_{tris}$ formulation (0.5 ug HA) generated titers which were several fold higher than the non-entrapped antigen control at 0.5 or 5 ug HA.

Taken together, the results showed that reduction of lipid content in the formulations to about 2 mg does not affect the adjuvant effect of liposomes.

The adjuvant effect of the vaccine aspects of the present invention is seen from the results in Tables 1, 2 and 3 as to sterol liposomes, Tables 4, 5 and 6 as to DMPC/cholesterol liposomes, Table 7 as to sterol liposomes, DMPC/cholesterol liposomes and DMPC/cholesterol liposomes containing DMPG and Table 8 as to both sterol and DMPC/cholesterol liposomes.

DEFINITIONS USED IN THE DESCRIPTION OF THE PRESENT INVENTION

For purposes of clarity, throughout the discussion of the present invention, the following definitions will be used:

The term "lipid" as used herein shall mean any suitable material resulting in a bilayer such that a hydrophobic portion of the lipid material orients toward the interior of the bilayer while a hydrophilic portion orients toward the aqueous phase. Lipids further include highly hydrophobic compounds such as triglycerides, sterols such as cholesterol which can be incorporated into the bilayer. The term lipid may include fatty acids. Specific lipids are phospholipids such as phosphatidylcholine (PC), phosphatidylethanolamine (PE), distearoyl phosphatidylcholine (DSPC), phosphatidylserine (PS), phosphatidylglycerol (PG), phosphatidic acid (PA), phosphatidylinositol (PI), sphingomyelin (SPM), and the like, alone or in combination. The phospholipids can be synthetic or derived from natural sources such as egg or soy. Some synthetic phospholipids are dimyristoylphosphatidylcholine (DMPC) and dimyristoylphosphatidylglycerol (DMPG). Liposomes can also contain other steroid components such as polyethylene glycol derivatives of cholesterol (PEG-cholesterols), coprostanol, cholestanol, or cholestane, and combinations of PC and cholesterol. Liposomes may also contain glycolipids.

The term "stabile lipid" shall be understood to mean lipids which are resistant to oxidative catabolism initiated by changes in pH, temperature, oxygen free radicals (e.g., such as those produced by infiltrating immune cells during inflammatory reaction) or other stress of the physiological environment. It is to be understood that stabile is a property in the nature of a continuum whereby normal lipid rigidity is modified by a stabilizing process such as hydrogenation. Thus a stabile lipid is a lipid resistant to oxidative catabolism initiated by changes in pH, as well as resistant to temperature, oxygen free radicals or other stresses of the physiological environment and is not rapidly deconstructed at common physiologic pH ranges presented in the in vivo environment of use. Stabile lipids, when organized into liposomes, will maintain structural integrity for an extended period of time in the physiological environment after parenteral administration, particularly as compared to other liposomes.

The term "peptide-like" will be understood to mean short chain peptides as well as proteins, lipoproteins and glycoproteins, but will also, for convenience, include non-proteinaceous molecules for example, amino acid containing molecules. In certain embodiments, the peptide-like therapeutic agent may additionally comprise vitamins, steroids, azidothymidine, and free primaquine in addition to other agents. A preferred class of peptides are immunomodulators such as interleukins, colony stimulating factors and interferons. An additionally preferred class of proteins are antigens and immunogens such as are used in vaccines.

The term "native state configuration" will be understood to mean organization of a moiety, such as a peptide, as it is configured when present in situ, i.e, in the native state, to be distinguished from non-native state configuration (denatured) wherein the moiety may be altered as to bioactivity or immunoreactivity.

"Labile" peptide-like therapeutic agents as used herein refer to the propensity for destruction or denaturation of the therapeutic agent in an animal by reactions other than the intended therapeutic reactions.

The term "extended elaboration" as used herein is understood to mean the release of therapeutic agents from liposomal encapsulation over a period in excess of what would normally occur without the presence of stabile liposomes and generally in about 24 hours and in some embodiments as long as about 2 to 3 weeks.

"Structural integrity of liposomes" as used herein shall mean the substantial maintenance of the pharmaceutical activity of the encapsulated substance during a period of extended elaboration. This structural integrity is presumed to arise from the persistence of the bilayer arrangement of the lipid material comprising the liposomes and the concomitant substantial maintenance of an entrapped aqueous phase for the period of extended elaboration. Structural integrity may be imparted by forming liposomes from combinations of lipids comprising sufficient stabile lipid to maintain the required structure when challenged by the physiological conditions present in the subject animal.

"Antigen" shall mean a substance or material that is recognized specifically by antibody and/or combines with an antibody.

The term "epitope" will be understood to mean the smallest part of an antigen moiety recognizable by the combining site of an immunoglobulin.

"Immunogen" shall mean a substance or material (including antigens) that is able to induce an immune response alone or in conjunction with an adjuvant. Both natural and synthetic substances may be immungens. An immunogens will generally be a protein, peptide, polysaccharide, nucleoprotein, lipoprotein, synthetic polypeptide, or hapten linked to a protein, peptide, polysaccharide, nucleoprotein, lipoprotein or synthetic polypeptide or other bacterial, viral or protozoal fractions. It will be understood that "immunogen" includes substances (e.g., small peptides) which do not generate an immune response (or generate only a therapeutically ineffective immune response) unless associated with an adjuvant. This will be referred to as "adjuvant-obligatory" immunogens.

"Adjuvant" shall mean a substance or material to potentiate an immune response when used in conjunction with antigens and immunogens. Adjuvants are further used to elicit immune response sooner, or a greater response, or with less antigen or immunogen.

"Immune response" shall mean a specific response of the immune system of an animal to antigen or immunogen. Immune response may include the production of antibodies and cellular immunity.

"Immunization conditions" shall mean factors which affect an immune response including the amount and kind of immunogen or adjuvant delivered to a subject animal including a human, method of delivery, number of inoculations, interval of inoculations, the type of subject animal and its condition.

"Vaccine" shall mean pharmaceutical formulations able to induce immunity.

"Immunity" shall mean a state of resistance of a subject animal including a human to an infecting organism or substance. It will be understood that an infecting organism or substance is defined broadly and includes parasites, toxic substances, cancer cells and other cells as well as bacteria and viruses. A Therapeutically Effective Immunization Course will produce the immune response.

"Immunization dose" shall mean the amount of antigen or immunogen needed to precipitate an immune response. This amount will vary with the presence and effectiveness of various adjuvants. This amount will vary with the animal and the antigen, immunogen and/or adjuvant but will generally be between about 0.1 ug/ml or less to about 100 ug per inoculation. The immunization dose is easily determined by methods well known to those skilled in the art, such as by conducting statistically valid host animal immunization and challenge studies. See, for example, *Manual of Clinical Immunology*, H. R. Rose and H. Friedman, American Society for Microbiology, Washington, D.C. (1980). In some instances, several immunization doses including booster doses will be administered to provide immunity, which collectively will be termed "Therapeutically Effective Immunization Course".

"Priming" shall mean the stimulation of a primary (as opposed to a secondary or later) response by an animal to an immunogen. The primary response is characterized by the manufacture by the animal of antibody to the immunogen, and ideally by the generation of a population of B-lymphocytes that respond to secondary or later immunogenic challenge—even absent adjuvant—with a rapid and substantive production of antibodies. Based upon such response 1, 2, 3 or more booster doses of immunogen absent adjuvant will generate a therapeutically effective immune response to the immunogen.

A "dosage form" in the extended elaboration therapeutic aspect of the present invention will be understood to mean the pharmaceutical delivery of any pharmaceutically active compound including an antigen via any route of administration, but preferably including subcutaneous, topical, intramuscular, intradermic, intramammary, intraperitoneal and intra-ocular. The term "dosage form" in the immunogenic or vaccine aspect of the present invention will be understood to mean any pharmaceutical form of administering a vaccine including oral, subcutaneous, intramuscular, intra-ocular, administration and utilizing vaccines in live, attenuated or synthetic or partial forms along with adjuvants and optionally immunomodulators such as cytokines. The combinations of the foregoing elements are prepared so that the immunogenic dosage form is adapted to produce an immune response in the subject animal including a human as easily and effectively as possible. Dosage forms of the present invention also include unit dosage forms, i.e., dosage forms which are administered in individual units at a dosage effective for therapy or to elicit an immunological response.

DETAILED DESCRIPTION OF THE INVENTION

There are three aspects of the present invention. The first aspect relates to high integrity liposomes, preferably multilamellar liposomes and most preferably stabile plurilamellar vesicles (SPLV), comprising at least one stabile lipid and at least one peptide-like therapeutic agent associated with the liposome, adapted for parenteral administration to an animal, especially mammals, including humans. A second aspect of the present invention relates to certain stabile liposomes, for example, those comprising DMPC/cholesterol, in combination with an immunogenic dose of an immunogen and optionally, an aluminum adjuvant, adapted for use as a vaccine. In a third aspect of the present invention, additional vaccine forms are described comprising liposomes comprising an organic acid of a sterol in combination with an immunogenic dose of an immunogen.

I. Stabile Liposomes Adapted for Parenteral Administration

In the first aspect of the present invention, liposomes comprising a stabile lipid in combination with a therapeutic amount of a peptide-like therapeutic agent adapted for parenteral administration are presented.

Preferred liposomes for the extended elaboration therapeutic aspect of the present invention were prepared from fully hydrogenated soy phosphatidylcholine and cholesterol in ratios of from about 4:1 to about 1:1 (phosphatidylcholine:cholesterol mole ratio). These liposomes were administered to animals and the animals were then tested for retention of administered material for periods up to about 2 weeks post administration. Quite surprisingly, administered material was found to be present at the site of parenteral administration for up to two weeks or in certain cases, longer at a level of about 20% when administered via intramuscular or subcutaneous administration. The extended retention at the injection site has surprisingly facilitated extended release of peptides over this period, while maintaining much of the integrity of the administered material, particularly peptides. In certain cases preferred high integrity liposomes are comprised of DMPC/cholesterol or DSPC/cholesterol.

In this aspect of the present invention, the administration profile that is therapeutically indicated will be influenced by many considerations including the increasing ease of handling the stabile lipids, the therapeutic agent to be incorporated into the liposome, the site of administration of the liposome preparation, and the nature and condition of the animal being treated. It is clearly preferred that administration of the dosage forms of the high integrity aspect of the present invention which include peptide-like therapeutic agents is by the parenteral route, because the use of this route of administration makes maximal use of the extended elaboration characteristics of high integrity liposomes. By administering the agents by this parenteral route, peptide-like therapeutic agents in the stabile liposomes of the present invention may be released slowly over a period of time ranging from at least about one day, i.e., about 24 hours, to about 2 to 3 weeks.

In certain embodiments of the present invention, the structural integrity and consequently, the extended elaboration characteristics of the stabile liposomes will be maintained even if stabile lipid is admixed with a diluent lipid or secondary lipid which is not stabile. In the practice of the present invention liposomes of sufficient structural integrity for the intended use may be designed by varying the rigidity of lipid membrane constituents or by varying the proportion in which stabile lipid is admixed with a diluent or secondary lipid. In the instant invention modifications of these above noted procedures for making liposomes are required due to the high rigidity of stabile lipids. In the most stabile lipids—such as fully hydrogenated phosphatidylcholine—a lipid film in the preparation process may be solubilized in organic solvent at an elevated temperature often about 50–60° C. This increases the flexibility of the lipid and permits formulation of liposomes.

Stabile lipids of greater flexibility may be prepared by a variety of methods. Hydrogenation of lipid to less than full hydrogenation produces a lipid of increased but less than maximum rigidity. Additionally, fully or partially hydrogenated lipids or other stabile lipids may be admixed with unsaturated flexible lipids. Cholesterol may also be added. As an admixing material, however, cholesterol is unique in that it tends to make stabile lipids more flexible while conversely having the property of rendering flexible lipids more rigid. Cholesterol is a preferred admixing lipid to increase the flexibility of the stabile lipid component of the liposomes of this invention. Additionally, alpha-tocopherol may function as an admixing lipid.

High integrity liposomes of this invention may be incorporated with therapeutic agents by the methods well known in the art such as those of U.S. Pat. Nos. 4,522,803 and 4,588,578 and the Mayer article, supra. Particular embodiments in the practice of this invention are the incorporation of peptide therapeutic agents such as growth hormone or growth hormone releasing factor, among others, preferably in multi-lamellar (MLV) or stable plurilamellar (SPLV) vesicles. These vesicle forms are clearly preferred. While not being limited by way of theory, it is believed that the use of MLVs or SPLVs results in a liposome which will exhibit extended elaboration after parenteral administration.

The liposomal dosage forms of the present invention are preferably formulated using stable plurilamellar vesicles (SPLV) or multilamellar vesicles (MLV), including frozen and thawed multilamellar vesicles (FATMLV), as described, for example, in U.S. Pat. No. 4,522,803 to Lenk, et al., or as described in Bally et al., PCT Publication No. 87/00043, Jan. 15, 1987, entitled "Multilamellar Liposomes Having Improved Trapping Efficiencies", each of which references is incorporated herein by reference. Liposomes of these types are preferred because MLVs enhance the extended elaboration delivery of the therapeutic dosage forms of the present invention. Dosage forms of the present invention also include unit dosage forms which may be administered for therapeutic effect.

Particular benefits of the liposomes of this aspect of the present invention are the enhancement of drug entrapment upon formation of the liposomes, and the enhancement of the amount of drug per amount of lipid (loading). Additional benefits include the extended elaboration that liposomal dosage forms according to the present invention exhibit when administered parenterally other than intravenously, i.e., via intramuscular, intramammary, intradermal, intraperitoneal, intra-ocular or subcutaneous routes. Topical dosage forms may also be formulated to exhibit extended elaboration characteristics.

The entrapment of up to about 70% of available peptide-like therapeutic agents are obtainable by the instant method. It is important to note that peptide entrapment levels are dependent on the specific peptide-like therapeutic agents being entrapped.

Liposomes entrap an aqueous medium which is enclosed by the lipid bilayers. The aqueous medium can be for example, water or water containing a dissolved salt or buffer. Examples of such salts or buffers can be sodium chloride and phosphate buffered saline (PBS). Other buffers include but are not limited to borate, citrate, Tris-HCl(Tris-(hydroxymethyl)-aminomethane hydrochloride), and HEPES (N-2-hydroxyethyl piperazine-N1-2-ethane sulfonic acid). Buffers may be in the pH range of between about 2.0 and about 14.0. In certain embodiments, the preparations are hydrated with HEPES buffer (150 mM NaCl, 20 mM HEPES), pH 7.0, borate buffer (100 mM $Na_2HCO_3$, 50 mM $H_3BO_3$), pH 8.5, or citrate buffer (150 MM Na-citrate), pH 8.5, or 0.01M sodium carbonate buffer (pH 9–11).

The loading of liposomes with the peptide-like therapeutic agent is also enhanced by the use of stabile lipids in the practice of this invention. For example, when liposomes entrapping BSTH were formed in the presence of lipid:B-STH at 2:1 (lipid:peptide) the liposomes thus formed were 6.1:1 lipid:peptide as opposed to 16.2:1 for similar liposomes formed from unhydrogenated lipids. In another instance liposomes prepared from lipid:galactose-albumin (1.8:1 feed) yielded a lipid:galactose-albumin liposome of 4.3:1 as opposed to 7.1:1 for unhydrogenated liposomes at a similar lipid:galactose-albumin feed ratio. In another example, DSPC liposomes (DSPC is obtainable from Avanti Polar Lipids, Birmingham, Ala.), optionally mixed with cholesterol (preferably 7:3 mole ratio of phospholipid to cholesterol), were formed entrapping calcitonin. Calcitonin is available in many forms and analogues and derivatives of calcitonin are being developed or are now available. All such analogues and derivatives are understood to be included in the term calcitonin. The high integrity liposomes of this invention extended the presence of detectable calcitonin from about 1 hour for free calcitonin to about 3 to 7 days.

In a liposome-drug delivery system, the therapeutic agent is encapsulated in the liposome (either in the lipid or aqueous phase), preferably multi-lamellar vesicles (MLV) or stable plurilamellar vesicles (SPLV) and then administered to the subject being treated. For example, see Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179, Lenk, et al., U.S. Pat. No. 4,522,803, and Fountain et al., U.S. Pat. No. 4,588,578. Preferably, in order to take advantage of the extended elaboration characteristics of the liposomal dosage forms of the present invention, the dosage forms are administered parenterally via an intramuscular or subcutaneous route. The dosage forms of the present invention may also be administered via an intra-ocular, intramammary, intradermal or intraperitoneal route to produce a therapeutic dosage form having the characteristics of extended elaboration. In addition to the parenteral dosage forms, certain dosage forms of the present invention may be utilized in topical formulations for extended topical delivery.

The liposomes may be dehydrated, thereby enabling storage for extended periods of time until use. Standard freeze-drying equipment or equivalent apparatus may be used to dehydrate the liposomes. Liposomes may also be dehydrated simply by placing them under reduced pressure. Alternatively, the liposomes and their surrounding medium can be frozen in liquid nitrogen prior to dehydration. Dehydration with prior freezing may be performed in the presence of one or more protective sugars in the preparation, according to the process of Janoff et al., U.S. patent application Ser. No. 759,419, filed Jul. 26, 1985, entitled "Dehydrated Liposomes", incorporated herein by reference. Examples of protective sugars that may be used include, but are not limited to, trehalose, maltose, sucrose, glucose, lactose and dextran. When the dehydrated liposomes are to be used, rehydration is accomplished by methods which include simply adding an aqueous solution, e.g., distilled water, to the liposomes and allowing them to rehydrate.

The therapeutic agents of this invention are administered associated with liposomes, in admixture with a pharmaceutically-acceptable carrier selected with regard to the intended route of administration and standard pharmaceutical practice.

Therapeutic agents for incorporation into stabile liposomes of the present invention include pharmacoactive agents, diagnostic agents, biological response modifiers, e.g., immunomodulators, contrast agents, radioactive agents, drug targeting carrier agents such as galactose-albumin, and the like. Preferred agents are peptide-like therapeutic agents which include the peptide-like agents such as galactose-albumin carriers, immunomodulators (e.g., interleukins) and hormones (e.g., somatotropins). Particular therapeutic agents are understood to include analogues and derivatives of such agents including biologically active fragments unless otherwise indicated.

In many instances when administering the peptide-like therapeutic agents, maintenance of the native-state is important for therapeutic activity. In other instances, the native-state may not be as important. When using a protein merely as a proteinic macromolecule carrier of a therapeutic agent, maintenance of the native state of such protein is of lesser importance, so long as the carrying function is not substantially compromised. For example, albumin has been reportedly used as a "carrier protein" for therapeutic agents, particularly as linked to galactose ("galactose-albumin") or glucose ("glycosylated-albumin"), thus facilitating hepatic uptake when presented in liposomal form (e.g., U.S. Pat. No. 4,376,765). As used herein "galactose-albumin" (and similarly glucose-albumin) refers to the moiety of galactose (or glucose) joined to albumin. Such moiety—glucose or galactose/carrier protein—is useful in targeting a therapeutic agent at the liver. The moiety is preferentially taken up by the liver, and by covalently joining a therapeutic agent to the carrier protein the therapeutic agent is similarly taken up by the liver. By way of example, the therapeutic agents doxorubicin, daunorubicin, or primaquine may be joined to the carrier protein to then be concentrated in the liver, thus localizing the therapeutic action of the agent (in this case, anticancer and antiparasitic activity).

Pharmaceutical dosage forms of the present inventions may be comprised of liposomes and any suitable pharmaceutical carrier. A preferred class of carrier is aqueous including both distilled water and isotonic saline. Administration of high integrity liposomes may be accomplished by any usual route with particular reference to the preferred routes of administration. Preferred routes of parenteral administration as used herein refer to intramuscular, intramammary, intraperitoneal, subcutaneous and intraocular administration. However, dosages adapted to parenteral administration may be used in a variety of administration methods, especially including topical administration. The dosage forms of the present invention deliver a peptide-like therapeutic agent in extended elaboration for a period ranging from 24 hours up to 2 or 3 weeks which is especially advantageous in situations in which the need for extended duration administration are shown to be therapeutically advantageous.

Dosages for therapeutic agents associated with liposomes will often be about that of the therapeutic agent alone; dosages will be set by the prescribing medical professional considering many factors including the age, weight and condition of the patient and the pharmacokinetics of the agent and release characteristics of the agent from the high integrity liposomes of the present invention.

In certain dosage forms, standard pharmaceutical carriers as described above may be included with the therapeutic agent and the liposome. The ratio of therapeutic agent to carrier will naturally depend on the chemical nature, solubility, trapping efficiency, and stability of the therapeutic agent, as well as the dosage contemplated. For parenteral administration or injection via such parenteral routes as intraperitoneal, intramuscular, subcutaneous, intramammary or intraocular route, sterile solutions of the liposome composition are prepared. For intravenous use, the total concentration of solutes should be controlled to render the preparation isotonic. One of ordinary skill in the art will recognize to maximize the delivery of a therapeutic agent of the present invention by varying the lipid:peptide ratio as well as the type of peptide-like therapeutic agent as well as the liposome utilized.

In another example of their use, high integrity liposomes may be incorporated into a broad range of topical dosage forms including but not limited to gels, oils, emulsions and the like. For instance, the suspension containing the high integrity liposomes may be added to the aqueous phase as an ingredient in the liposome preparation. Such preparations may be administered as topical creams, pastes, ointments, gels, lotions and the like for direct application and are particularly advantageous for extended elaboration via a topical route.

The stabile liposomes of the present invention may be applied to other areas as well. For example, the present invention is readily adapted for use in the veterinary and animal husbandry areas. In the application of this invention to animal husbandry those skilled in the art will understand the use of high integrity liposomes in the administration of a number of therapeutic agents including growth promotants (e.g., growth hormone and growth releasing factor) as well as lactation promoting agents such as BSTH. Administration of such agents in therapeutically effective amounts can increase productivity. Dosage and administration of therapeutic agents, in this invention, presumes therapeutically effective amounts. Therapeutically effective amounts of therapeutic agents as used herein will mean that amount of therapeutic agent that produces therapeutic action. This amount will be understood to vary with the particular agent or analog or derivative thereof, the condition being treated, the site, manner and duration of administration and other considerations well known to those skilled in the art.

The stabile liposomes of the present invention may also be adapted for use as vaccines. In the application of this therapeutic delivery invention to the vaccine art, the necessary dosage will be understood to be an immunogenic dosage. It will be understood that an immunogenic amount of an antigenic entity such as GM2 is that amount which will stimulate the response cells of a subject animal (if in the GM2 example a human is presumed to be the subject animal then a response cell is a B-cell) to produce immunoglobulins against the antigen (here, GM2). This amount will vary with the potency of adjuvant, with the mode of administration and with the type and condition of animal but is easily determined by any of the well known tests for immunoglobulins with an increase in immunoglobulin representing immunogenic response. In some embodiments, liposomes of this invention, especially DMPC/cholesterol liposomes, in association with antigens and immunogens, function as adjuvants.

II. Vaccines

A. DMPC/Cholesterol Liposomes

In a second aspect of the present invention, certain stabile liposomes of the present invention have shown surprising activity as vaccines. A preferred class of lipids for forming liposomes in this vaccine aspect of the present invention are those of dimyristoylphosphatidylcholine and cholesterol ("DMPC/cholesterol"). In this second aspect, liposomes comprising DMPC/cholesterol and an immunogenic amount of an immunogen or antigen are utilized as vaccines.

DMPC/cholesterol forms the required liposomes which may be multilamellar or unilamellar over a wide range of proportions from about 100:1 (molar) to about 20:80. More preferred is about 70:30 to about 30:70, and most preferred is about 70:30. Additionally other lipids may be admixed with DMPC/cholesterol, such as dimyristoylphosphatidylglycerol, dicetyl phosphate, phosphatidic acid, phosphatidylethanolamine, phosphatidylcholine and cholesterol hemisuccinate ("CHS"), such as those with sodium ("$CHS_{sodium}$") or tris(hydroxymethyl) aminomethane ("$CHS_{tris}$") as the counter ion. In certain cases, the use of a negatively charged lipid, for example, DMPG or dicetyl phosphate may actually result in a decrease in the adjuvancy of the compositions. However, these compositions still show utility for use in the present invention.

The DMPC/cholesterol containing vaccines may additionally comprise aluminum compounds as adjuvants. Aluminum compounds are adjuvants well known in the art, and include aluminum hydroxide, aluminum phosphate, aluminum oxide or aluminum sulfate and will be termed collectively aluminum adjuvants. By way of example, aluminum hydroxide is widely used in diphtheria and tetanus toxoid vaccines as well as in veterinary applications. Aluminum hydroxide powder spontaneously forms a gel upon hydration. To prepare a vaccine containing aluminum hydroxide, commonly immunogen in aqueous buffer is added to the preformed gel. Such vaccines are referred to as being aluminum-adsorbed.

DMPC/cholesterol multilamellar liposomes of the SPLV process are preferred but any other type of liposome may be used. Preferably, the liposome is at least about 1 micron in diameter. The SPLV process generally involves rotoevaporation of lipids in solvent in a round bottom flask to form a thin film. The lipid film is then dispersed in a non-water miscible solvent such as ether or methylene chloride to which the aqueous solute (containing immunogen) is then added. The mixture is then sonicated while being dried by a stream of nitrogen gas which drives off the organic solvent. The resultant liposome paste is resuspended in aqueous buffer. U.S. Pat. No. 4,522,803 to Lenk, et al. further describes this process and is incorporated herein by reference. If desired the resulting liposomes may be filtered or sized such as by passing through a filter stack such as a 0.4 or 0.2um filter (Nuclepore, Pleasanton, Calif.).

The resulting liposomes are conveniently administered in aqueous material. The volume of aqueous material will vary with the particular liposome to be administered and is not critical. Generally about 0.5 ml is a convenient liposome dosage volume. Typically better adjuvant response is observed with greater amounts of lipid.

B. Salt Forms of Organic Acid Derivatives of Sterols as Vaccines

In a third aspect of the present invention, it has now been discovered that salt forms of organic acid derivatives of sterols are particularly useful pharmaceutical adjuvants. Such adjuvants are conveniently used in the form of liposomes.

In preferred embodiments of this vaccine aspect of the present invention the liposomes containing salt forms of organic acid derivatives will generally have a total net negative charge, i.e. the charged species generally represents substantially about 100% by weight of the lipid portion of the liposome. In particularly preferred embodiments of the present invention, the negatively charged lipid species represents 100% by weight of the lipid portion of the liposome and the liposome comprises a single lipid species, for example, CHS and other cholesterol ester or ether derivatives containing 100% negative residues. Charged and particularly substantially negatively charged liposomes of the present invention display surprisingly superior adjuvancy to many neutral liposomes and even liposomes containing amounts of negatively charged lipids of the prior art. A particularly preferred class of lipids for forming liposomes are those of cholesterol hemisuccinate ("CHS"), such as those with sodium ("$CHS_{sodium}$") or tris(hydroxymethyl) aminomethane ("$CHS_{tris}$") as the counter ion, which are generally negatively charged.

Of course, it is recognized by those of ordinary skill in the art that certain liposome forming lipids may be added to the steroidal negatively charged lipids of the present invention to produce liposomal vaccines according to the present invention without substantially decreasing the immunogenicity of these vaccine dosage forms. For example, in certain embodiments, DMPC/cholesterol may be added to the liposomes without substantially impacting immunogenicity.

Salt forms of an organic acid derivative of a sterol may be used in the practice of the invention. Generally any sterol which can be modified by the attachment of an organic acid may be used in the practice of the present invention. For example, such sterols include but are not limited to cholesterol, cholesterol derivatives, vitamin D, phytosterols (including but not limited to sitosterol, campesterol, stigmasterol, and the like), steroid hormones, and the like.

Exemplary organic acids which may be used to derivatize the sterols include but are not limited to, the carboxylic acids, dicarboxylic acids, polycarboxylic acids, hydroxy acids, amino acids and polyamino acids. Because the salt forms increase the water solubility of organic acids, any organic acid may be used to derivatize the sterols; however an advantage may be obtained if the organic acid moiety itself is water soluble. Such water soluble organic acid moieties include but are not limited to water-soluble aliphatic carboxylic acids such acetic, propionic, butyric, valeric acids and the like (N.B., up to four-carbon acids are miscible with water; the five-carbon free acid is partly soluble and the longer chain free acids are virtually insoluble); water-soluble aliphatic dicarboxylic acids such as malonic, succinic, glutaric, adipic, pimelic, maleic and the like (N.B., the shorter chains are appreciably more soluble in water; borderline solubility in water occurs at C6 to C7); and water-insoluble aromatic dicarboxylic acids such as hemimellitic, trimesic, succinimide, and the like; polycarboxylic acids; water-soluble hydroxy acids such as glycolic, lactic, mandelic, glyceric, malic, tartaric, citric, and the like (N.B., alpha-hydroxy acids containing a branched chain attached to the alpha-carbon of the carbonyl group would be less susceptible to hydrolysis and, therefore, advantageous in the practice of the present invention); and any of the amino acids and polyamino acids.

The organic acid can be linked to an hydroxyl group of the sterol via an ester or an ether bond using conventional methods (see, for example, U.S. Pat. Nos. 3,859,047; 4,040,784; 4,042,330; 4,183,847; and 4,189,400). The salt forms of the derivatized sterols can be prepared by dissolving both the organic acid derivative of the sterol and the counterion of the salt (e.g., the free base of the salt) in an appropriate volatile solvent, and removing the solvent by evaporation or a similar technique leaving a residue which consists of the salt form of the organic acid derivative of the sterol. Counterions that may be used include, but are not limited to, tris, 2-amino-2-methyl-1,3-propanediol, 2-aminoethanol, bis-tris propane, triethanolamine, and the like to form the corresponding salt. In fact, the free base of an ionizable bioactive agent such as miconazole free base and the like may also be used as the counterion.

CHS forms liposomes when added to an aqueous material. This can conveniently be performed at 20–25° C. (room temperature) and atmospheric pressure. Agitation accelerates the process of liposome formation and is performed by such methods as vortexing, sonication or other methods well known in the art. If desired, the resulting liposomes may be filtered or sized such as by passing through a filter stack such as a 0.4 or 0.2 um filter (Nuclepore, Pleasanton, Calif.). Any method available in the art for forming CHS containing liposomes may be used in the present invention including the methods described herein and the methods set forth, for example, in Janoff, et al., PCT Publication No. WO 85/04578, published Oct. 24, 1985 entitled "Steroidal Liposomes" and U.S. patent application Ser. No. 110,286 of Swenson, et al., entitled, "Aqueous Preparation of Liposome Composition," filed Oct. 19, 1987 which are incorporated by reference herein. Typically better adjuvant response is observed with greater amounts of lipid and with multilamellar vesicles. Suitable aqueous material is saline solution, buffered solution, dextrose solution, bovine serum albumen or other well known aqueous pharmaceutical diluents.

C. Characteristics Common to Both DMPC/Cholesterol and Sterol Liposomes as Vaccines In formulating the vaccines of the present invention typical aqueous materials used in the pharmaceutical industry may be used. Suitable aqueous material for either sterol or DMPC/cholesterol liposomes is saline solution, buffered solution, dextrose solution or other well known aqueous pharmaceutical diluents.

The DMPC/cholesterol or sterol vaccine liposomes of the present invention are conveniently associated with an immunogenic amount of antigen or immunogen. This association is produced by mixing, adsorption, encapsulation, co-formation or other methods well known in the art.

Vaccines of the present invention are conveniently administered in a dosage form. The dosage forms including liposomal dosage forms resulting from the method of the present invention can be used therapeutically in mammals, including man, in the treatment of infections or conditions which require the delivery of immunogen in its bioactive form. Such conditions include but are not limited to disease states such as those that can be treated with vaccines.

Dosage forms of this immunogenic aspect of the present invention may also include different lipid phases (including micelles) of the adjuvant as well as gels for example, adjuvant gels including aluminum gels, liquid crystals, powders, precipitates and solutions. In particular embodiments the dosage form can be a unit dosage form configured and adapted to a single administration.

The dosage forms including liposomal dosage forms resulting from the method of the present invention can be used therapeutically in animals such as mammals, including man, in the treatment of infections or conditions which require the delivery of immunogen in its bioactive form. Such conditions include but are not limited to disease states such as those that can be treated with vaccines. Extracorporeal treatment of immunoresponsive tissues is also contemplated.

Dosage forms also include micelle forms of the adjuvant as well as adjuvant incorporated into gel such as aluminum gels, liquid crystals, powders, precipitates and solutions. In particular embodiments, the dosage form can be a unit dosage form configured and adapted to a single administration. Aluminum adjuvants are used in forms and proportions well known to those skilled in the art. Commercial preparations of aluminum hydroxide gel containing vaccines such as tetanus toxoids range from about 0.2 to about 1 mg of aluminum/ml. The safe upper range is far higher for human vaccines with as much as 15 mg or more of aluminum hydroxide per dose are known with no limit for veterinary applications.

The mode of administration of the immunogenic dosage form may determine the sites and cells in the organism to which the dosage form will be delivered. The dosage forms including liposomal dosage forms of the present invention can be administered alone but will generally be administered in admixture with a pharmaceutical carrier selected with regard to the intended route of administration and standard pharmaceutical practice. The dosage forms may be injected parenterally, for example, intra-arterially or intravenously. The dosage forms may also be administered via oral, subcutaneous, or intramuscular routes. For parenteral administration, the dosage forms can be used, for example, in the form of a sterile aqueous solution which may contain other solutes, for example, enough salts or glucose to make the solution isotonic. Other uses, depending upon the particular properties of the preparation, may be envisioned by those skilled in the art.

For administration to humans in the preventive or curative treatment of disease states responding to vaccine therapy, the prescribing physician will ultimately determine the appropriate dosage for a given human subject, and this can be expected to vary according to the age, weight, and response of the individual as well as the nature and severity of the patient's disease. The dosage of the drug in liposomal dosage form will generally be about that or less than that employed for the free drug. In some cases, however, it may be necessary to administer dosages outside these limits.

The following examples are provided for purposes of illustration only and are not to be viewed as a limitation of the scope of the invention.

EXAMPLE 1
Preparation of High Integrity Stable Plurilamellar Liposomes

A solution of 14 g of bovine somatotrophic hormone (BSTH) in 140 ml carbonate buffer, pH 10.9 was prepared. Then 21.1 g of hydrogenated soy phosphatidylcholine in powdered form and 6.9 g of cholesterol in powdered form were dissolved in 50 ml chloroform and dried to powder by rotoevaporation. The lipid film thus formed was resuspended in 140 ml diethyl ether and placed in a round bottom flask, and sonicated in a water bath at 47° C. during addition of the BSTH in buffer. Sonication was continued until substantially all ether was evaporated. A stream of 20° C. nitrogen was then applied to the resulting material until residual ether was removed.

The resulting material was then resuspended in 800 ml of buffer at 47–50° C. and the liposomes therein washed two times by repeated centrifugation at approximately 20,000 times gravity for 30 minutes. The washed liposomes were then resuspended to a final volume of 164 ml. The resulting high integrity liposome suspension contained 27.5 mg BSTH/ml, 128.0 mg HSPC/ml and 42.0 mg cholesterol/ml.

EXAMPLE 2
Increasing Milk Production

The liposome preparation of Example 1 was administered to cows at two 350 mg doses per cow with the second dose two weeks after the original dose. This regimen produced a 14.9% increase in milk production as compared to untreated cows. Furthermore, as compared to cows treated with daily injection of 12.5 mg free BSTH, two injections of BSTH in hydrogenated soy phosphatidylcholine liposomes was 28.8% as effective. Liposomes of unhydrogenated soy phosphatidylcholine, delivered in 3 weekly doses of 175 mg BSTH over three weeks, were only 15.7% as effective as daily doses.

EXAMPLE 3
Extended Elaboration/Retention of High Integrity Liposomes In Situ
Preparation:

6.0 g of BSTH was dissolved on 60.0 ml of carbonate buffer pH 9.4. Powdered HSPC, 3.52 g and powdered cholesterol, 1.73 g were dissolved in 20 ml chloroform in a 500 ml round bottom flask. To this solution was added $1.2 \times 10^6$ dpm of 3H-dipalmitoyl phosphatidylcholine. The lipids were then dried by rotoevaporation, and resuspended in 75 ml diethyl ether. The flask and contents were then placed in a 45° C. water bath sonicator. The BSTH solution was then added to the diethyl solution while sonicating as the ether evaporated. After 15 minutes residual ether was removed by applying a stream of nitrogen to the contents of the flask. The contents of the flask was then resuspended in 150 ml carbonate buffer and the resulting liposomes washed two times by centrifugation and brought up to a final volume of 34.0 ml.
Elaboration/Retention:

A 0.320 ml dose of the liposome suspension was injected intramuscularly (leg) into each of 30 Swiss-Wistar mice. This corresponded to $9.77 \times 10^5$ dpm per animal. Three mice were sacrificed at each time point over a period of 27 days. The percentage of radioactivity remaining at the site of injection was compared to similar injection of unhydrogenated liposomes (egg phosphatidylcholine with egg phosphatidylethanolamine). Radioactivity in the mice receiving high integrity liposomes was still present after 27 days while the radioactivity of the unhydrogenated liposomes had almost entirely dissipated.

EXAMPLE 4
Extended Elaboration/Retention of High Integrity Liposomes In Situ Preparation: 0.75 g of BSTH were dissolved in 15 ml carbonate buffer, pH 10.9. 1.13 g of HSPC and 0.37 g of cholesterol are dissolved in 5 ml chloroform. The mixture was dried under rotoevaporation as in Example 3, and the lipid resuspended in 20 ml of diethyl ether, and placed in a round bottom flask.

The flask and contents were placed in a 47° C. water bath sonicator, the sonicator turned on, and then the BSTH in the aqueous phase was added. Sonication was continued until the weight of the mixture was equal to the additive weights of the dried lipid film and the aqueous phase. A stream of nitrogen gas was then applied to remove any residual ether. The contents of the flask was then resuspended in 40 ml of carbonate buffer at 47–50° C. and the liposomes therein were washed two times by repeated centrifugation at approximately 20,000 times gravity for 30 minutes. The liposome suspension was then brought to a final volume of 11.1 ml.

The effect of these liposomes was a substantial weight gain over 28 days by hypophysectomized rats (75–85 gm/rat) administered BSTH in the high integrity liposomes as compared to hypophysectomized rats administered single identical amounts of 80 ug/day (2,400 ug in total per animal) injected i.m. in the hind leg of BSTH in unhydrogenated liposomes.

EXAMPLE 5
IL-2 Retention and Release 67.0 mg HSPC and 33.0 mg cholesterol were dried from chloroform by rotoevaporation in a round bottom flask. Then 5 ml of anhydrous diethyl ether was added to the flask. To this was added 1 mg of IL-2 in 1 ml of 5 mM ammonium acetate (pH5), 0.9% sodium chloride along with $6.0 \times 10^5$ DPM of $^3$H-IL-2. The resulting dispersion of aqueous solution in ether was sonicated in a water bath at 45°–50° C. and simultaneously dried with a stream of nitrogen gas until no trace of ether was detectable by smelling. To the resulting dried liposome paste was added to 10 ml of phosphate buffered saline. The mixture was vortexed vigorously to remove any material that had adhered to the flask wall. Aliquots of this mixture were taken for tritium counting.

The remaining mixture, a liposome suspension, was centrifuged for 20 minutes in a J-20 rotor (Beckman Instruments, Mountainview, Calif.) at 10,000 rpm. The supernatant was removed and an additional 10 ml of phosphate buffered saline was used to resuspended the liposomes of the pellet.

Table A, below, shows the substantial period (14 days) during which IL-2 remains at the injection site in mice receiving 2.7 mg/kg in 10 mg of high integrity liposomes. Table B, below shows that the retention was accompanied by persistence of available bioactive interleukin. Such persistence is seen to be quite pronounced as compared to free interleukin or to liposomal interleukin with other than high integrity liposomes.

TABLE A

I.M. Slow Release of $^3$H Labelled Peptides
From HSPC/C Liposomes in Mice

| Time After Injection | % of Dose Remaining at Injection Site |
|---|---|
| 1 Hr | 84.4% |
| 3 Hrs | — |
| 1 Day | 78.1% |
| 3 Days | — |
| 4 Days | 64.9% |
| 5 Days | — |
| 7 Days | 69.4% |
| 9 Days | — |
| 10 Days | 58.9% |
| 12 Days | — |
| 14 Days | 28.1% |
| 19 Days | — |
| 23 Days | — |
| 27 Days | — |

TABLE B

Recovery of "Bioactive" Peptide (IL-2) At the Injection Site

| | % of Initial Bioactive IL-2 Ramaining At Injection Site | | |
|---|---|---|---|
| Time | Free IL-2 | IL-2-EPC SPLV | IL-2-HSPC/Chol SPLV |
| 1 Hr | 2.1 | 53.5 | 52 |
| 1 Day | ND | 15 | 44 |
| 4 Days | ND | 4.8 | 20 |
| 7 Days | ND | 1.3 | 11 |
| 10 Days | ND | ND | 18 |
| 14 Days | ND | ND | 14 |

EXAMPLE 6
Galactose-Albumin-Primaquine

HSPC:Cholesterol liposomes were prepared according to the method of Example 1. Briefly, lipid in chloroform was dried as a thin film on the bottom of a round bottom flask by rotoevaporation. 5 ml of diethyl ether were added to the flask and the lipid dislodged from the flask walls by swirling. In this example the material to be entrapped was human serum albumin conjugated to tritiated galactose ("galactose-albumin") and primaquine ("galactose-albumin-primaquine"). The galactose-albumin-primaquine in 0.3 ml of aqueous solution was added to the 5 ml of ether-lipid mixture.

Conjugate formation was effected by simultaneous sonication and drying of the mixture using a gentle stream of nitrogen. Sonication and drying were discontinued when no odor of ether could be detected. The conjugate material was in the form of a paste which was washed with 10–20 ml of phosphate buffered saline (PBS). This was accomplished by adding PBS to the flask and vortexing vigorously to remove all residues from flask walls. The resulting liposome suspension was then centrifuged at 4° C. for 10–20 minutes at 10,000 rpm (J-20 Centrifuge, JA-20 rotor, Beckman, Palo Alto, Calif.). The resulting supernatant was poured off and the pellet resuspended in fresh PBS, vortexed and centrifuged again under the same conditions two times to remove non-entrapped material.

193 mg of the resulting encapsulated containing $10^7$ disintegrations per minute material was injected intramuscularly into the hind leg of mice. The retention of high integrity liposomes containing galactose-albumin can be seen from Table C and Table D, below to be at least 14 days. Table C discloses the retention at site of injection of radioactivity for up to 14 days when the radioactive material was encapsulated in high integrity liposomes, while, in contrast, free radioactive material was eliminated in a single day. Table D discloses that injected encapsulated material remaining at the site of injection retains bioactivity for an extended period as compared to the activity retention of unencapsulated material.

TABLE C

I.M. Slow Release of $^3$H Labelled Peptides
From HSPC/Chol Liposomes in Mice

| | % of Dose Remaining at the Injection Site | |
|---|---|---|
| Time After Injection | HSPC Galactose-Albumin | Free Galactose-Albumin |
| 1 Hr | 109 | 55.7 |
| 7 Hrs | | 29.75 |
| 1 Day | 107 | 25.5 |
| 1.75 Days | | 11.23 |
| 2.75 Days | | 5.8 |
| 3 Days | 97 | |
| 5 Days | 75 | |
| 5.75 Days | | 1.8 |
| 7 Days | 59 | |
| 10 Days | 47 | |
| 14 Days | 23 | |

TABLE D

Change in Fragmentation of Peptide
Following Liposome Encapsulation

| | % of Peptide At Injection Site that Is Fragmented | |
|---|---|---|
| Time After Injection | Free Galactose-Albumin-Primaquine | HSPC/C Encapsulated Galactose-Albumin Primaquine |
| 1 Hr | 16 | 1 |
| 7 Hrs | 87 | 1 |
| 2 Days | 100 | 1 |
| 3 Days | 100 | 7 |
| 5 Days | 100 | 15 |
| 7 Days | 100 | 21 |
| 10 Days | 100 | 17 |
| 14 Days | 100 | 16 |

EXAMPLE 7
Calcitonin-DSPC 8.27 mg DSPC (1:1 initial L:D ratio) and 1.73 mg cholesterol (7:3 mole % ratio DSPC: cholesterol), both in chloroform, were transferred to a 50 ml round bottom flask. The lipids were dried to a film under vacuum using rotoevaporation. The lipids were then solubilized in 0.500 ml methanol with heating for 1–2 mins. in a 60° C. water bath. Ten milligrams of calcitonin (Mitsubishi Chemical Co., Japan MCI-536) was solubilized in 0.100 ml sodium acetate buffer. This solution was added to the solvent mixture. The solvent was removed under vacuum, using rotoevaporation in a 60° C. water bath. Once the solvent was removed, the lipid/drug film was resuspended in 0.5 ml 60° C. sodium acetate buffer. The preparation was washed by addition of 0.5 ml of 60° C. sodium acetate buffer followed by centrifugation at 12,100×g for 10 minutes. The supernatant was decanted and the liposomal pellet resuspended with 1 ml of 60° C. sodium acetate buffer. The suspension was again centrifuged at 12,100×g for 10 minutes and resuspended. The resuspended DSPC-cholesterol lipomes containing calcitonin were administered s.c. to mice to compare retention of the liposomal preparation to that of free calcitonin. Free calcitonin was undetectable after one hour in mice. The calcitonin of liposomes of the instant invention was at least about 70% present one day after administration and persisted for about 3 to 7 days disclosing a substantial increase in retention time over free calcitonin.

EXAMPLE 8
Preparation of Adjuvant Liposomes (CHST, Low Lipid) with Antigen (HAB)

50 mg of $CHS_{tris}$ (powdered) were placed into a 15 ml test tube. 100 ul of bromelain fragment of HA in aqueous buffer was added (673 ug HAB, 0.01M phosphate buffered saline in 0.9% NaCl). The mixture was intermittently vortexed over a 2 hour period at 22.5° C.+/−2.5° C. and left until no large clumps were visible. The resultant MLV liposomes were washed 3 times in 10 ml of aqueous buffer solution being separated each time by 15 minutes of centrifugation (10,000 rpm, J-20 rotor (Beckman, Palo Alto, Calif.)). The final pellet was brought to 4.0 ml in buffer and sealed in an amber vial under nitrogen.

EXAMPLE 9
Preparation of Adjuvant Liposomes (CHST) with Antigen (HA)

500 mg of $CHS_{tris}$ (powdered) were placed into a 15 ml test tube. 1 ml of HA in aqueous buffer was added (300 ug HA, 0.01M phosphate buffered saline in 0.9% NaCl). The mixture was intermittently vortexed over a 2 hour period at 22.5° C.+/−2.5° C. The resultant MLV liposomes were washed 3 times in 10 ml of aqueous buffer solution being separated each time by 15 minutes of centrifugation (10,000 rpm, J-20 rotor (Beckman, Palo Alto, Calif.)). The final pellet was brought to 4.0 ml in buffer and sealed in an amber vial under nitrogen.

EXAMPLE 10
Preparation of Adjuvant Liposomes (CHST, High Lipid) with Antigen (HAB)

500 mg of $CHS_{tris}$ (powdered) were placed into a 15 ml test tube. 1 ml of bromelain fragment of HA in aqueous buffer was added (673 ug HAB, 0.01M phosphate buffered saline in 0.9% NaCl) The mixture was intermittently vortexed over a 2 hour period at 22.5° C.+/−2.5° C. The resultant MLV liposomes were washed 3 times in 10 ml of aqueous buffer solution being separated each time by 15 minutes of centrifugation (10,000 rpm, J-20 rotor). The final pellet was brought to 4.0 ml in buffer and sealed in an amber vial under nitrogen.

EXAMPLE 11
Preparation of Adjuvant Liposomes (CHST) with Antigen (HAB)

500 mg of $CHS_{tris}$ (powdered) were placed into a 15 ml test tube. 2 ml of bromelain fragment of HA in aqueous buffer was added (1,100 ug HAB, 0.9% NaCl). The mixture was intermittently vortexed over a 2 hour period at 22.5° C.+/−2.5° C. The resultant MLV liposomes were washed 3 times in 10 ml of 0.9% NaCl solution being separated each time by 15 minutes of centrifugation (10,000 rpm, J-20 rotor). The final pellet was brought to 4.0 ml in buffer and sealed in an amber vial under nitrogen.

EXAMPLE 12
Preparation of Adjuvant Liposomes (Very High Lipid) with Antigen (HAB)

1500 mg of $CHS_{tris}$ (powdered) were placed into a 15 ml test tube. 3 ml of bromelain fragment of HA in aqueous buffer was added (673 ug HAB, 0.01M phosphate buffered saline in 0.9% NaCl) The mixture was intermittently vortexed over a 2 hour period at 22.5° C.+/−2.5° C. The resultant liposomes were washed 3 times in 10 ml of aqueous buffer solution being separated each time by 15 minutes of centrifugation (10,000 rpm, J-20 rotor). The final pellet was brought to 4.0 ml in buffer and sealed in an amber vial under nitrogen.

EXAMPLE 13
Preparation of Adjuvant Liposomes (CHST) with Antigen (HAB)

200 mg of $CHS_{tris}$ was weighed into a 15 ml Corex tube. 2 ml of HAB (1,100 ug in 0.01M phosphate buffered saline in 0.9% NaCl) was added to the lipid in the tube. The lipid in aqueous mixture was kept at room temperature for approximately 2 hours with intermittent vortexing until no large clumps were visualized microscopically. 10 ml of buffer was added to the liposomes. The liposomes were vortexed vigorously and were transferred to a 15 ml Corex tube. The MLV liposomes were washed 3 times in 10 ml of buffer, being separated each time by 10 minutes of centrifugation (10,000 rpm, J-20 rotor, Beckman, Palo Alto, Calif.). The final liposome pellet was brought to 4.0 ml in buffer and sealed in an amber vial under nitrogen.

EXAMPLE 14
Preparation of Adjuvant Liposomes (CHST, MPLA) with Antigen (HAB)

200 mg of $CHS_{tris}$ was weighed into a 500 ml round bottomed flask. The lipid was solubilized in 10 ml warm (45° C.) methanol and 6 mg of Monophosphoryl Lipid A (purchased from Ribi) was added. The mixture was dried by rotoevaporation. 2 ml of HAB (1,100 ug in 0.01M phosphate buffered saline in 0.9% NaCl) was added to the flask. The mixture was swirled and vortexed for approximately 1 hour until the lipid was fully hydrated and was removed from the sides of the flask. 10 ml of buffer was added to the liposomes. The liposomes were vortexed vigorously and were transferred to a 15 ml. Corex tube. The MLV liposomes were washed 3 times in 10 ml of buffer, being separated each time by 10 minutes of centrifugation (10,000 rpm, J-20 rotor, Beckman, Palo Alto, Calif.). The final liposome pellet was brought to 4.0 ml in buffer and sealed in an amber vial under nitrogen.

EXAMPLE 15
Preparation of Adjuvant Liposomes (CHSNa) with Antigen (HAB)

500 mg of $CHS_{sodium}$ (powdered) were placed into a 15 ml test tube. 1 ml of bromelain fragment of HA in aqueous buffer was added (673 ug HAB, 0.01M phosphate buffered saline in 0.9% NaCl) The mixture was intermittently vortexed over a 2 hour period at 22.5° C.+/−2.5° C. The resultant MLV liposomes were washed 3 times in 10 ml of aqueous buffer solution being separated each time by 15 minutes of centrifugation (10,000 rpm, J-20 rotor). The final pellet was brought to 4.0 ml in buffer and sealed in an amber vial under nitrogen.

EXAMPLE 16
Preparation of Adjuvant Liposomes (DMPC/Chol) with Antigen (HA)

100 mg of cholesterol and 400 mg of DMPC were placed into a 500 ml round bottom flask and suspended in 3 ml chloroform and dried to a film by rotoevaporation. 20 ml of anhydrous ether was added to the flask followed by 1.5 ml of HA in aqueous buffer was added (915 ug HA, 0.01M phosphate buffered saline in 0.9% NaCl)—"aqueous buffer"). The mixture was covered loosely with foil and sonicated in a 40° C. water bath while concurrently evaporating the ether with a gentle stream of nitrogen gas. The resultant lipid paste was thoroughly dried under nitrogen until no trace of ether was noted by smell. 10 ml of buffer was added to the flask and the liposome suspension was transferred to a 15 ml test tube. The resultant liposomes were washed 3 times in 10 ml of aqueous buffer being separated each time by 10 minutes of centrifugation (10,000 rpm, J-20 rotor (Beckman, Palo Alto, Calif.)). The final pellet was brought to 6.0 ml in buffer and sealed in an amber vial under nitrogen.

EXAMPLE 17
Preparation of Adjuvant Liposomes (DMPC/Chol) with Antigen (HAB)

100 mg of cholesterol and 400 mg of DMPC were placed into a 500 ml round bottom flask and suspended in 3 ml chloroform and dried to a film by rotoevaporation. 20 ml of anhydrous ether was added to the flask. 1.5 ml of HAB in aqueous buffer was added (1,000 ug HAB, 0.01M phosphate buffered saline in 0.9% NaCl). The mixture was covered loosely with foil and sonicated in a 40° C. water bath while concurrently evaporating the ether with a gentle stream of nitrogen gas. The resultant lipid paste was thoroughly dried under nitrogen until no trace of ether was noted by smell. 10 ml of aqueous buffer was added to the flask and the liposome suspension was transferred to a 15 ml test tube. The resultant liposomes were washed 3 times in 10 ml of aqueous buffer solution being separated each time by 10 minutes of centrifugation (10,000 rpm, J-20 rotor (Beckman, Palo Alto, Calif.)). The final pellet was brought to 6.0 ml in buffer and sealed in an amber vial under nitrogen.

EXAMPLE 18
Preparation of Adjuvant Liposomes (DMPC/Chol 40:60 Mole Percent) with Antigen (HAB)

92 mg of cholesterol and 108 mg of DMPC were placed into a 100 ml round bottom flask and suspended in 3 ml chloroform and dried to a film by rotoevaporation. 10 ml of anhydrous ether was added to the flask. 2.0 ml of HAB in aqueous buffer was added (1,100 ug HAB, 0.01M phosphate buffered saline in 0.9% NaCl). The mixture was covered loosely with foil and sonicated in a 40° C. water bath while concurrently evaporating the ether with a gentle stream of nitrogen gas. The resultant lipid paste was thoroughly dried under nitrogen until no trace of ether was noted by smell. 10 ml of buffer was added to the flask and the liposome suspension was transferred to a 15 ml test tube. The resultant liposomes were washed 3 times in 10 ml of aqueous buffer solution being separated each time by 10 minutes of centrifugation (10,000 rpm, J-20 rotor (Beckman, Palo Alto, Calif.)). The final pellet was brought to 6.0 ml in buffer and sealed in an amber vial under nitrogen.

EXAMPLE 19
Preparation of Adjuvant Liposomes (DMPC/Chol 70:30 Mole Percent) with Antigen (HAB)

40 mg of cholesterol and 160 mg of DMPC were placed into a 100 ml round bottom flask and suspended in 3 ml chloroform and dried to a film by rotoevaporation. 10 ml of anhydrous ether was added to the flask. 2.0 ml of HAB in aqueous buffer was added (1,100 ug HAB, 0.01M phosphate buffered saline in 0.9% NaCl). The mixture was covered loosely with foil and sonicated in a 40° C. water bath while concurrently evaporating the ether with a gentle stream of nitrogen gas. The resultant lipid paste was thoroughly dried under nitrogen until no trace of ether was noted by smell. 10 ml of buffer was added to the flask and the liposome suspension was transferred to a 15 ml test tube. The resultant liposomes were washed 3 times in 10 ml of aqueous buffer solution being separated each time by 10 minutes of centrifugation (10,000 rpm, J-20 rotor (Beckman, Palo Alto, Calif.)). The final pellet was brought to 6.0 ml in buffer and sealed in an amber vial under nitrogen.

EXAMPLE 20
Preparation of Adjuvant Liposomes (DMPC/Chol 50:50) with Antigen (HAB)

72 mg of cholesterol and 128 mg of DMPC were placed into a 100 ml round bottom flask and suspended in 2 ml chloroform and dried to a film by rotoevaporation. 10 ml of anhydrous ether was added to the flask. 2.0 ml of HAB in aqueous buffer was added (1,100 ug HAB in 0.01M phosphate buffered saline in 0.9% NaCl) with the ether. The resulting mixture of aqueous solution and lipid in ether was covered loosely with foil and sonicated in a 40° C. water bath while concurrently evaporating the ether with a gentle stream of nitrogen gas. The resultant lipid paste was thoroughly dried under nitrogen until no trace of ether was noted by smell. 10 ml of buffer was added to the flask and the liposome suspension was vigorously vortexed and transferred to a 15 ml COREX tube. The resultant liposomes were washed 3 times in 10 ml of aqueous buffer solution being separated each time by 10 minutes of centrifugation (10,000 rpm, J-20 rotor (Beckman, Palo Alto, Calif.)). The final pellet was brought to 4.0 ml in buffer and sealed in an amber vial under nitrogen.

EXAMPLE 21
Preparation of Adjuvant Liposomes (DMPC/Chol 30:70 Mole Percent) with Antigen (HAB)

114 mg of cholesterol and 86 mg of DMPC were placed into a 100 ml round bottom flask and suspended in 2 ml chloroform and dried to a film by rotoevaporation. 10 ml of anhydrous ether was added to the flask. 2.0 ml of HAB in aqueous buffer was added (1,100 ug HAB in 0.01M phosphate buffered saline in 0.9% NaCl) with the ether. The resulting mixture of aqueous solution and lipid in ether was covered loosely with foil and sonicated in a 40° C. water bath while concurrently evaporating the ether with a gentle stream of nitrogen gas. The resultant lipid paste was thoroughly dried under nitrogen until no trace of ether was noted by smell. 10 ml of buffer was added to the flask and the liposome suspension was vigorously vortexed and transferred to a 15 ml COREX tube. The resultant liposomes were washed 3 times in 10 ml of aqueous buffer solution being separated each time by 10 minutes of centrifugation (10,000 rpm, J-20 rotor (Beckman, Palo Alto, Calif.)). The final pellet was brought to 4.0 ml in buffer and sealed in an amber vial under nitrogen.

EXAMPLE 22
Preparation of Adjuvant Liposomes (DMPC/Chol 50:50 Mole Percent at High Lipid) with Antigen (HAB)

This preparation was prepared as described in Example 21 except that 320 mg DMPC and 180 mg Cholesterol were added to the flask and the amount of HAB was 1010 ug (1.5 ml).

EXAMPLE 23
Preparation of Adjuvant Liposomes (DMPC/Chol 50:50 Mole Percent at Low Lipid) with Antigen (HAB)

This preparation was prepared as described in Example 21 except that 32 mg DMPC and 18 mg Cholesterol were weighed out into a 25 ml round bottom flask; lipids were resuspended in 0.5 ml chloroform, dried, resuspended in 5 ml anhydrous ether and mixed with 150 ul of HAB (1,010 ug). After preparation of liposomes, the final pellet was brought to 2.5 ml.

EXAMPLE 24
Preparation of Gel Admixed with Liposomes

Aluminum hydroxide gel, 2% (Alhydrogel™) containing 7.29 mg/ml aluminum was used in conjunction with 1.02 ml of the liposomes of this invention prepared as in Example 18. The liposomes were admixed with 0.67 ml aluminum hydroxide gel and 5.31 ml of saline. The final aluminum concentration was 0.7 mg/ml and the HAB concentration was 10 ug/ml. The mixture was sealed in a glass vial with rubber stopper and crimp seal.

EXAMPLE 25
Preparation of Adjuvant Liposomes Containing DMPG with Antigen (HAB)

60 mg of cholesterol, 126 mg of DMPC and 14 mg of DMPG were placed into a 100 ml round bottom flask and suspended in 3 ml chloroform and dried to a film by rotoevaporation. 5 ml of anhydrous ether was added to the flask. 2.0 ml of HAB in aqueous buffer was added (1,100 ug HAB in 0.01M phosphate buffered saline in 0.9% NaCl) to the flask with the ether. The resulting mixture of aqueous solution and lipid in ether was covered loosely with foil and sonicated in a 45° C. water bath while concurrently evaporating the ether with a gentle stream of nitrogen gas. The resultant lipid paste was thoroughly dried under nitrogen until no trace of ether was noted by smell. 10 ml of buffer was added to the flask and the liposome suspension was vigorously vortexed and transferred to a 15 ml COREX tube. The resultant liposomes were washed 3 times in 10 ml of aqueous buffer solution being separated each time by 10 minutes of centrifugation (10,000 rpm, J-20 rotor (Beckman, Palo Alto, Calif.)). The final pellet was brought to 4.0 ml in saline, filtered under pressure through a 0.4 um and a 0.2 um filter and sealed in an amber vial under argon.

EXAMPLE 26
Preparation of Adjuvant Liposomes Containing DMPG and Lipid A with Antigen (HAB)

The preparation was formulated as described in example 25 except that 6 mg Lipid A (Sigma) was added to the flask together with DMPC, cholesterol and DMPG.

EXAMPLE 27
Preparation of Adjuvant Liposomes Containing DMPG and Monophosphoryl Lipid A with Antigen (HAB)

The preparation was formulated as described in example 25 except that 6 mg Monophosphoryl Lipid A (Ribi) was added to the flask together with DMPC, cholesterol and DMPG.

EXAMPLE 28
Preparation of Adjuvant Liposomes Containing DMPG. Monophosphoryl Lipid A and Aluminum Gel with Antigen (HAB)

The preparation was formulated as described in example 27 except that in the final step aluminum hydroxide gel was mixed as described in example 24.

EXAMPLE 29
Adjuvancy Tested

Liposomes containing HAB were prepared as in the examples. Entrapment values were determined by SRID and the liposomes were diluted in saline to a concentration of 10 ug protein/ml and were sealed in a glass vial with a rubber stopper and crimp seal.

For each composition, five 450–500 g male Hartley guinea pigs (Buckberg Lab Animals, Landis Store, Pa.) were injected intramuscularly with 0.5 ml of the liposome suspension or with 0.5 ml of free HAB in the right hind leg (5 ug). In certain cases, the guinea pigs were injected with 0.5 ml of vaccine (HA, 5 ug). At 4 weeks post immunization, the guinea pigs were lightly anaesthetized with ether and approximately 4 ml of blood was drawn by cardiac puncture. The blood was allowed to clot at room temperature overnight. The blood was centrifuged, and the serum was drawn off and stored at 4° C. until tested. The day after bleeding, the guinea pigs were again injected i.m. with 0.5 ml of HA or free or liposomal HAB (5 ug), this time in the left hind leg. Blood was collected in the same manner at 6 and 8 weeks after the initial injection.

Total anti-HA IgG antibodies in the serum samples were determined by Enzyme Immunoassay (EIA) and neutralizing antibodies were determined by Hemagglutination Inhibition Assay (HAI) as described in the following example. The results for the composition of Example 9 are shown in Tables 1, 2 and 3. The results for the composition of Example 17 are shown in Tables 4, 5 and 6.

Certain of the above-described examples were tested for adjuvancy as described above to determine the relative adjuvancy of DMPC/cholesterol liposomes, CHS liposomes and DMPC/cholesterol liposomes which contained substantial quantities of negatively charged lipids described in the prior art. The results of the adjuvancy tests are presented in Table 7.

The results set forth in Table 7 indicate that DMPC/cholesterol (neutral liposome) and CHS liposomes (providing a substantially total net negative charge) produced significantly greater adjuvancy than DMPC/cholesterol liposome preparations containing quantities of negatively charged lipid, i.e., DMPG. It is important to note that DMPG containing liposomes produced significantly reduced adjuvancy than for liposomes which did not contain DMPG. We note that the use of negatively charged lipids in DMPG containing liposomes produced an enhanced response relative to a purified HA fragment (HAB). However, quite surprisingly, the CHS liposomes (substantially totally negative) and DMPC/cholesterol (neutral) liposomes which did not contain DMPG produced unexpectedly enhanced adjuvant activity.

The results indicate that the incorporation of DMPG in liposomes may have marginally increased the immunogenicity of HAB relative to HAB alone, but when combined in DMPC/cholesterol liposomes, the DMPG appears to have actually reduced the adjuvancy of the DMPC/cholesterol.

The surprisingly enhanced activity of the compositions of the present invention evidence that the use of DMPC/cholesterol and CHS liposomes can increase the adjuvancy more than 10,000 times, an unexpected result not disclosed in the prior art.

EXAMPLE 30

Analytical Procedures

A. Hemagglutination Inhibition Assay (HAI)

25 ml of buffer (0.01M phosphate buffered saline in 0.9% NaCl, 0.05% sodium azide) was added to well numbers 2 through 12 of each row of a 96 well u-bottom microtiter plate (Costar, Cambridge, Mass.) Serum samples to be tested were diluted 1:10 in buffer and 25 ul was placed in wells 1 and 2 in duplicate rows. Samples were serially diluted 2-fold across the plate. 25 ul of Influenza hemagglutinin (HA, B/Ann Arbor Subunit Concentrate pool, Connaught Laboratories, Inc., Swiftwater, Pa.; 160 HA Units/ml) was added to all wells. The plate was gently agitated and was incubated at about 20–25° C. for 30 minutes. 50 ml of a 0.5% washed chicken red blood cell (RBC) suspension was added to all wells. The plate was again agitated and was allowed to set at 20–25° C. for 30–40 minutes or until a control well containing RBC's alone forms a compact pellet (negative pattern). The plate is tilted 45° and the serum titer endpoint is reported as the last well dilution forming a negative pattern.

B. Enzyme Immunoassay Procedure (EIA)

200 ul of a 1ug/ml solution of Influenza HA (B/Ann Arbor Subunit Zonal Concentrate Pool, Connaught Laboratories, Inc., Swiftwater, Pa.) was added to all wells of a 96 well flat bottom plate (Immuno-Plate I, NUNC, Denmark). Plates were covered and refrigerated overnight. The plates were emptied, 200 ul of 1% bovine serum albumin (BSA) in 0.1M phosphate buffered saline (PBS) was added, and the plates were incubated at 37° C. for 23 hours. Plates were washed twice with PBS and 100 ul of serum/Tween (75% calf serum in PBS containing 0.2% sodium azide and 0.05% Tween-20) was added to all wells. All standards and serum samples were diluted in serum/Tween where necessary and 100 ul of each was added to triplicate wells. Plates were covered and incubated at 37° C. for 2 hours and were washed twice with PBS. 200 ul of rabbit anti-guinea pig IgG-horseradish peroxidase conjugate (Cappel, Cooper Biomedical, Malvern, Pa.; 1:20,000 in 10% calf serum in 0.5× PBS) was added to all wells and the plates were incubated at 37° C. for 2 hours. The plates were emptied and 200 ul 0.1% Tween-20 in 1% BSA was added. After 3 minutes, this step was repeated. The plates were washed 4 times with water and 200 ul of orthophenylenediamine (OPD) substrate (0.0014M citric acid, 0.027M dibasic sodium phosphate, 0.006% hydrogen peroxide) was added to each well. The plates were incubated 45 minutes in the dark and 50 ul of 0.03% sulfuric acid was added to all wells. The plates were read at 494 nm (Titertek Multiskan, Flow Laboratories, McLean, Va.) and serum titers were read off of the standard curve.

C. Quantitation of Entrapped HAB (or HA) by Single Radial Immuno-Diffusion (SRID)

Immunoreactive HAB was quantitated by SRID using hyperimmune rabbit anti-HA antibody (Connaught Laboratories, Inc., Swiftwater, Pa.). Gels (1% agarose (Seakem) (FMC Bio Products, Rocklane, Me.) in 0.1M phosphate buffered saline/0.05% Sodium Azide) containing 3 ul antibody per ml were prepared in 230×115×1.5 mm molds. Liposome samples and standards were diluted in Zwitlergent 314™ detergent (Cal Biochem—Behring Corp., LaJolla, Calif.) to a final concentration of 1.5% detergent and were incubated at 37° C. for 1 hour. 15 ul of treated samples were loaded in duplicate into 4 mm wells punched into the agar. The gel was incubated in a humid chamber at 20–25° C. temperature for 20–24 hours. The gel was transferred to GelBond™ type transparent mounting plastic (FMC Bio Products, Rockland, Me.) and was dried by pressing with weighted blotter paper. The gel was stained with Coomassie brilliant blue and background stain was removed with destain. Precipitin ring diameters were measured using a micrometer and light box. Samples were quantitated by linear regression of the square diameters of the standard samples.

EXAMPLE 31

Melanoma Procedures

Liposomes containing ganglioside GD3 (kindly provided by Dr. P. Livingston, Sloan-Kettering, New York, N.Y.) were prepared at 10:1 and 100:1 (w/w) lipid to antigen (GD3) ratio using 10 mg lipid to 1 mg GD3 and 150 mg lipid to 1.5 mg GD3. Liposomes were prepared using either $CHS_{tris}$ or DMPC/cholesterol (70:30 mole percent).

GD3 antigen suspended in phosphate buffered saline (PBS but without Ca++ or Mg++) at pH 7.2 was entrapped in either $CHS_{tris}$ lipid liposomes or DMPC/cholesterol (70:30 mole percent) lipid liposomes. $CHS_{tris}$/GD3 MLV liposomes were made by Method A (below) and DMPC/cholesterol/GD3 SPLV liposomes by Method B (below).

Mice were injected 4 times with the liposomal antigen preparation and antibody level tested. Antibody to melanoma GD3 was produced. It was noted however that other melanoma vaccine preparations yielded higher antibody titers in mice than the instant preparation by the regimen described herein.

Method A 10 mg $CHS_{tris}$ (powdered) and 1 mg GD3 (10:1 ratio) in 50 ul PBS were placed in a test tube and hydration of lipids allowed for 2 hours at room temperature with intermittent vortexing. The lipid material was resuspended in 10 ml PBS without Ca++ or Mg++ and centrifuged at 13,000 rpm for 30 minutes, two times. The final liposome pellet was resuspended in 2.5 ml PBS. The liposome preparation was sealed in an amber vial under nitrogen until testing. An additional formulation at 100:1 lipid/antigen ratio was prepared as above, using 150 mg $CHS_{tris}$ and 1.5 mg GD3 in 300 ul PBS.

Method B 2 mg cholesterol and 8 mg DMPC in 0.5 ml chloroform were dried by rotoevaporation in a 25 ml round-bottom flask, resolubilized in 2 ml anhydrous ether and mixed with GD3 in 60 ul PBS. The resulting mixture was sonicated at 40° C. under a stream of N2 to form a lipid paste which was further dried under N2. The dry material was resuspended in 10 ml PBS and centrifuged at 10,000 rpm for 10 minutes, three times. The final liposome pellet was brought to 2.28 ml and supplemented with Alhydrogel (0.7 mg Al/ml). An additional formulation at 100:1 lipid/antigen ratio was prepared as above using 120 mg DMPC, 30 mg cholesterol, and 1.5 mg GD3 in 0.45 ml PBS.

EXAMPLE 32

Additional Immune Response Studies

To determine further the role of the dose of both HA (split antigen) and lipid, guinea-pigs were inoculated with liposome formulations at 5 or 0.5 ug HA each entrapped in various amount of lipid (Table 8). Two $CHS_{tris}$ formulations were prepared as described in Example 9 to give a dose of 5.0 ug HA and either 13.6 mg lipid (MLV, $CHS_{tris}$, H) or 1.9 mg lipid (MLV, $CHS_{tris}$, L). The "H" and "L" designations refer to high and low amount of lipid in particular dosages. The demarcation of high and low is arbitrary but convenient in conceptualizing any role that the relative amount of lipid plays in vaccine efficacy.) Two DMPC/CHOL formulations were prepared as described in Example 16 to give a dose of 5.0 mg HA and either 9.7 mg lipid (SPLV, DMPC/C, H) or 2.9 mg lipid (SPLV, DMPC/C, L).

In addition, each H formulation exhibiting a relatively high amount of lipid per 0.5 ml inoculum was further diluted 1:10 in PBS and the resulting suspensions containing 0.5 ug HA and either 1.4 mg $CHS_{tris}$ or 1.0 mg DMPC/CHOL also inoculated in the same trial.

Inoculation of guinea pigs and determination of antibody by EIA or HAI were performed as described in Examples 29 and 30. The results (Table 8) showed that 5 mg HA in $CHS_{tris}$ liposomes induced a strong adjuvant effect regardless whether this amount of antigen was entrapped in 13.6 or 1.9 mg of lipid. The same observation can be made in the case of DMPC/CHOL formulations.

Furthermore, 1:10 dilution of $CHS_{tris}$ formulation (0.5 ug HA) generated titers which were several fold higher than the non-entrapped antigen control at 0.5 or 5 ug HA. Taken together, the results showed that reduction of lipid content in the formulation does not affect the adjuvant effect of liposomes.

This invention has been described in terms of specific embodiments set forth in detail herein, but it should be understood that these are by way of illustration and the invention is not necesarily limited thereto. Modifications and variations will be apparent from the disclosure and may be resorted to without departing from the spirit of the inventions those of skill in the art will readily understand. Accordingly, such variations and modifications are considered to be within the purview and scope of the invention and the following claims.

TABLE 1

Immunogenicity Enhancement of HA and HAB via Steroidal Adjuvant
ANTI-HA ANTIBODY TITERS (Units/ml)

| Formulation | Example No. | Dose (ug) | Starting Lipid Concentration (mg) | Primary 4 week | | Secondary 6 week | | 8 week | | 12 week | | 25 week | | 52 week | |
|---|---|---|---|---|---|---|---|---|---|---|---|---|---|---|---|
| | | | | EIA | HAI | EIA | HAI | EIA | HAI | EIA | HAI | EIA | HAI | EIA | HAI |
| A. | | | | | | | | | | | | | | | |
| HA | | 5.0 | NA | 24.9 | 28.6 | 527.3 | 1810.2 | 306.4 | 452.6 | 141.3 | 226.3 | 92.4 | 148.9 | — | 100.8 |
| HA in CHS-TRIS MLV's | 2 | 5.0 | 500 | 853.9 | 1338.1 | 4047.9 | 9667.5 | 2520.8 | 1140.9 | 1039.2 | 1280.0 | 610.1 | 1280.0 | — | 403.2 |
| HA | | 0.5 | NA | 0.9 | 5.0 | 103.4 | 190.3 | 43.5 | 31.3 | 29.6 | 40.0 | 29.5 | 40.0 | — | 23.7 |
| HA in CHS-TRIS MLV's | 2 | 0.5 | 500 | 52.2 | 52.8 | 2643.8 | 8914.4 | 1669.0 | 2228.6 | 861.9 | 1114.3 | 624.1 | 970.1 | — | 640.0 |
| B. | | | | | | | | | | | | | | | |
| HAB | | 5.0 | NA | 0.4 | 5.0 | 1.8 | 5.0 | 1.4 | 5.0 | <1.5 | 9.1 | 1.4 | 6.3 | — | 5.0 |
| HAB in Complete Freund's Adjuvant | | 5.0 | NA | 1225.6 | 105.6 | 3775.6 | 1522.2 | 3739.2 | 452.6 | 2335.4 | 452.6 | 789.6 | 196.0 | — | 67.3 |
| HAB in CHS-Na MLV's | 6 | 5.0 | 500 | 128.5 | 151.1 | 2446.8 | 6755.9 | 1655.9 | 2281.7 | 722.0 | 1016.4 | 394.2 | 538.2 | — | 320.0 |
| HAB in CHS-TRIS MLV's | | 5.0 | 56 | 3.5 | 5.0 | 882.4 | 557.2 | 604.3 | 278.6 | 229.1 | 139.3 | — | — | — | — |
| HAB in CHS-TRIS MLV's | | 5.0 | 167 | 16.4 | 8.7 | 3064.9 | 1594.5 | 1324.1 | 350.6 | 557.7 | 452.6 | — | — | — | — |
| HAB in CHS-TRIS MLV's | 3 | 5.0 | 500 | 59.0 | 72.8 | 2383.1 | 2474.5 | 1038.6 | 1388.1 | 293.4 | 485.0 | 146.3 | 309.3 | — | 160.0 |
| HAB in CHS-TRIS MLV's | 5 | 5.0 | 1500 | 669.8 | 301.1 | 3442.7 | 5120.0 | 1991.5 | 1280.0 | 593.6 | 844.5 | — | — | — | — |
| Control | | 0 | NA | 0.1 | 5.0 | 0.1 | 5.0 | 0.2 | 5.0 | <0.3 | 5.0 | 0.1 | 5.0 | — | 5.0 |

Legend
Liposomes containing HA or HAB were prepared at the indicated lipid concentrations. (Example formulations are indicated)
Entrapment values were determined by single radial immuno-diffusion (SRID) and liposomes were diluted in saline to a dosage of 0.5 or 5 ug per 0.5 ml dose. Hartley guinea pigs were injected IM at 0 and 4 weeks. At the indicated timepoints, blood was collected by cardiac puncture. Serum antibody titers (total anti-HA IgG and neutralizing antibodies) were determined by EIA and HAI assay, respectively. Values represent the geometric mean of 3–5 guinea pigs per group.

TABLE 2

Effect of Liposome Entrapment of HAB on the Ability to Prime the Immune System
ANTI-HA ANTIBODY TITERS (Units/ml)

| Immunization | | Dose (ug) | Primary 4 week | | Secondary 6 week | | 8 week | | 12 week | | 23 week | | 52 week | |
|---|---|---|---|---|---|---|---|---|---|---|---|---|---|---|
| Primary | Boost | | EIA | HAI | EIA | HAI | EIA | HAI | EIA | HAI | EIA | HAI | EIA | HAI |
| Experiment I | | | | | | | | | | | | | | | |
| HAB | HAB | 15 | 0.6 | 5.0 | 21.8 | 5.0 | 25.1 | 5.0 | 29.8 | 7.9 | 15.0 | 5.0 | 0.6 | 5.0 |
| Liposomal HAB | Liposomal HAB | 5 | 27.9 | 11.1 | 2706.4 | 1416.6 | 1287.1 | 1846.1 | 584.5 | 842.3 | 250.5 | 380.6 | 266.5 | 250.4 |
| Liposomal HAB | Liposomal HAB | 15 | 336.5 | 253.9 | 4112.7 | 2031.9 | 1060.8 | 2031.9 | 819.2 | 1280.0 | 312.5 | 320.0 | 258.8 | 226.3 |
| HAB | Liposomal HAB | 5 | 0.2 | 5.0 | 84.0 | 7.1 | 59.6 | 20.0 | 24.6 | 12.6 | 14.1 | 7.9 | 3.3 | 10.0 |
| Liposomal HAB | HAB | 5 | 7.7 | 6.6 | 711.1 | 595.6 | 397.5 | 932.1 | 169.7 | 595.6 | 154.5 | 269.1 | 97.6 | 269.1 |
| HA | HA | 5 | 11.6 | 16.8 | 719.4 | 466.1 | 266.0 | 500.8 | 166.8 | 134.5 | 24.9 | 40.0 | 18.5 | 31.8 |

TABLE 2-continued

Effect of Liposome Entrapment of HAB on the Ability to Prime the Immune System
ANTI-HA ANTIBODY TITERS (Units/ml)

| Immunization | | Dose | Primary | | Secondary | | | | | | | | | |
|---|---|---|---|---|---|---|---|---|---|---|---|---|---|---|
| | | | 4 week | | 6 week | | 8 week | | 12 week | | 23 week | | 52 week | |
| Primary | Boost | (ug) | EIA | HAI | EIA | HAI | EIA | HAI | EIA | HAI | EIA | HAI | EIA | HAI |
| Experiment II | | | | | | | | | | | | | | |
| HAB | HAB | 5 | 0.4 | 5.0 | 1.8 | 5.0 | 1.4 | 5.0 | <1.5 | 9.1 | 1.4 | 6.3 | — | 5.0 |
| Liposomal HAB | Liposomal HAB | 5 | 59.0 | 72.8 | 2383.1 | 2474.5 | 1038.6 | 1388.1 | 293.4 | 485.0 | 146.3 | 309.3 | — | 160.0 |
| HA | HA | 5 | 24.9 | 28.6 | 527.3 | 1810.2 | 306.4 | 452.6 | 141.3 | 226.3 | 92.4 | 148.9 | — | 100.8 |
| Liposomal HAB | HAB | 5 | 26.9 | 10.0 | 1096.4 | 1208.4 | 561.5 | 320.0 | 326.2 | 250.4 | — | — | — | — |
| HA | HAB | 5 | 19.9 | 13.0 | 223.7 | 640.0 | 155.1 | 148.9 | 64.6 | 113.1 | — | — | — | — |

Legend
Liposomes containing HAB were prepared from CHS as in example 3. Entrapment value was determined by SRID and liposomes were diluted in saline to a dosage of 5 or 15 ug protein per 0.5 ml dose. Hartley guinea pigs ware injected IM at 0 time and boosted at 4 weeks. At the indicated timepoints, blood was collected by cardiac puncture. Serum antibody titers (total anti-HA IgG and neutralizing antibodies) were determined by EIA and HAI assay, respectively. Values represent the geometric mean of 4–5 guinea pigs per group.

TABLE 3

Steroidal adjuvant effect after mixing or entrapping HAB
ANTI-HA antibody titers (Units/ml)

| | Primary | | Secondary | | | | | |
|---|---|---|---|---|---|---|---|---|
| | 4 week | | 6 week | | 8 week | | 12 week | |
| Formulation | EIA | HAI | EIA | HAI | EIA | HAI | EIA | HAI |
| HA | 29.6 | 23.4 | 683.6 | 556.3 | 370.3 | 294.8 | 173.8 | 254.0 |
| HAB | 0.2 | 5.0 | 0.6 | 5.0 | 0.8 | 5.0 | 0.7 | 5.0 |
| HAB in CHS-Tris MLV's | 49.8 | 57.7 | 1998.3 | 842.3 | 1188.5 | 640.0 | — | — |
| HAB + CHS-Tris MLV's | 1.6 | 5.7 | 731

TABLE 5

Enhancement of Immunogenicity of HA by use of DMPC/cholesterol SPLV's

| | | Primary | | | | Secondary | | | | | | | |
|---|---|---|---|---|---|---|---|---|---|---|---|---|---|
| | Dose | 4 week | | 6 week | | 8 week | | 12 week | | 25 week | | 52 week | |
| Formulation | (ug) | EIA | HAI | EIA | HAI | EIA | HAI | EIA | HAI | EIA | HAI | EIA | HAI |
| HA | 0.5 | 0.9 | 5.0 | 103.4 | 190.3 | 43.5 | 31.3 | 29.6 | 40.0 | 29.5 | 40.0 | — | 23.7 |
| Liposomal HA | 0.5 | 72.6 | 26.4 | 1938.3 | 3469.8 | 1561.7 | 905.1 | 28.2 | 354.1 | 429.3 | 269.1 | — | 105.3 |
| HA | 5.0 | 24.9 | 28.6 | 527.3 | 1810.2 | 306.4 | 452.6 | 141.3 | 226.3 | 92.4 | 148.9 | — | 100.8 |
| Liposomal HA | 5.0 | 349.1 | 398.6 | 5480.1 | 8914.4 | 3649.7 | 3189.1 | 2233.9 | 1940.1 | 1121.8 | 864.6 | — | 320.0 |

Legend:
DMPC/cholesterol SPLV's (70:30 mole ratio) containing HA were prepared as in Example 1. Entrapment values were determined by SRID and Liposomes were diluted in saline to a dosage of 0.5 or 5.0 ug per 0.5 ml dose. Hartley guinea pigs were injected i.m. at 0 and 4 weeks. At the indicated time points, blood was collected by cardiac puncture. Serum antibody titers
(total anti-HA IgG and neutralizing antibodies were determined by EIA and HAI assay, respectively. Values represent the geometric mean of 4–5 guinea pigs per group.

TABLE 6

Enhancement of Immunogenicity of HAB by use of DMPG:Cholesterol SPLV's and Aluminum Hydroxide gel.

| | | Starting | Primary | | | | Secondary | | | | | | | | |
|---|---|---|---|---|---|---|---|---|---|---|---|---|---|---|---|
| | Dose | Lipid | 4 week | | 6 week | | 8 week | | 12 week | | 25 week | | 52 week | | |
| Formulation | (ug) | Concentration | EIA | HAI | EIA | HAI | EIA | HAI | EIA | HAI | EIA | HAI | EIA | HAI | |
| Experiment I | | | | | | | | | | | | | | | |
| HAB | 5.0 | NA | 0.3 | 5.0 | 5.9 | 5.7 | 2.5 | 5.0 | | | | | | | |
| Liposomal HAB | 5.0 | 200 | 15.6 | 7.6 | 596.5 | 60.6 | 132.8 | 30.3 | | | | | | | |
| Liposomal HAB in Aluminum hydroxide gel | 5.0 | 200 | 18.5 | 9.4 | 1093.7 | 80.0 | 123.4 | 30.3 | | | | | | | |
| Liposomal HAB | 5.0 | 500 | 54.6 | 32.8 | 2738.4 | 183.8 | 460.1 | 100.0 | | | | | | | |
| Liposomal HAB in Aluminum hydroxide gel | 5.0 | 500 | 48.7 | 15.2 | 7546.1 | 297.8 | 557.5 | 100.8 | | | | | | | |
| EXPERIMENT II | | | | | | | | | | | | | | | |
| HAB (in saline) | 5.0 | NA | 0.4 | 5.0 | 1.8 | 5.0 | 1.4 | 5.0 | <1.5 | 9.1 | 1.4 | 6.3 | — | 5.0 | |
| Liposomal HAB | 5.0 | 500 | 18.3 | 11.5 | 363.7 | 183.8 | 163.8 | 47.6 | — | — | — | — | — | — | |
| Liposomal HAB in Aluminum hydroxide gel | 5.0 | 500 | 73.3 | 34.8 | 1045.8 | 970.1 | 435.4 | 422.2 | 172.9 | 242.5 | 178.3 | 302.1 | — | 40.0 | |
| Liposomal HAB in Aluminum hydroxide gel | 0.5 | 500 | 1.8 | 5.0 | 335.9 | 163.8 | 102.7 | 60.6 | 22.7 | 63.5 | — | — | — | — | |

Legend:
DMPC: Cholesterol SPLV's (70:30 mole ratio) containing HAB were prepared at the indicated lipid concentrations. The liposomes in Experiment II were sterile filtered through a 0.4/0.2 um filter stack. Entrapment values were determined by SRID and liposomes were diluted in saline or aluminum hydroxide gel and saline to a dosage of 0.5 or 5 ug per 0.5 ml dose. Hartley guinea pigs were injected i.m. at 0 and 4 weeks. At the indicated timepoints, blood was collected by cardiac puncture. Serumantibody titers (total anti-HA IgC and neutralizing antibodies) were determined by EIA and HIA assay, respectively. Values represent the geometric mean of 4–5 guinea pigs per group.

TABLE 7

Anti-HA ANTIBODY (U/ml)

| | Example and Formulation | 4 Week | | 6 Week | | 8 Week | |
|---|---|---|---|---|---|---|---|
| | | EIA | HAI | EIA | HAI | EIA | HAI |
| | Vaccine (Split) | 50.26 | 34.27 | 345.19 | 250.41 | 203.73 | 160.00 |
| | HAB | 0.09 | 5.00 | <0.12 | 5.00 | <0.13 | 5.95 |
| | HAB + Gel | 0.13 | 5.00 | 1.83 | 5.00 | 7.98 | 5.00 |
| 19 | D, C 70:30* | 16.36 | 64.47 | 425.09 | 177.07 | 160.97 | 125.21 |
| 20 | D, C 50:50 | 0.73 | 5.96 | 63.92 | 34.82 | 43.65 | 18.88 |
| 18 | D, C 40:60 | 11.00 | 10.99 | 465.50 | 80.00 | 167.16 | 82.39 |
| 21 | D, C 30:70 | 18.69 | 5.00 | 492.20 | 56.57 | 259.93 | 36.34 |
| 23 | D, C 50:50 L | 7.12 | 4.00 | 171.04 | 5.00 | 119.25 | 5.00 |
| 22 | D, C 50:50 H | 31.13 | 23.40 | 200.10 | 47.57 | 88.97 | 40.00 |
| 25 | D, C, Dg | 0.33 | 5.00 | 2.45 | 5.00 | 1.78 | 8.66 |
| 26 | D, C, Dg, LA | 0.26 | 5.00 | 3.71 | 7.07 | 2.68 | 8.41 |
| 27 | D, C, Dg, mpLA | 0.43 | 5.00 | 18.03 | 7.07 | 16.61 | 8.41 |
| 28 | D, C, Dg, mpLA + Gel | 2.93 | 10.00 | 1077.60 | 139.29 | 647.21 | 139.29 |
| 14 | CHST, mpLA | 2.57 | 6.59 | 223.83 | 47.57 | 156.92 | 37.22 |
| 13 | CHST | <3.11 | 5.00 | 666.24 | 67.27 | 176.01 | 95.14 |
| 8 | CHST, L | 4.90 | 5.00 | 958.32 | 421.14 | 529.58 | 201.59 |
| 10 | CHST, H | 76.00 | 65.75 | 2330.36 | 708.28 | 1343.14 | 421.14 |

D = DMPC; C = Cholesterol; Dg = DMPG; CHST = cholesterol hemisuccinate TRIS salt; LA = Lipid A; mpLA = monophosphoryl Lipid A; L = low lipid; H = high lipid; Gel = Al(OH)$_3$ gel; * = molar ratio.

TABLE 8

ANTI-HA ANTIBODIES IN SERA OF MICE IMMUNIZED WITH HA ENTRAPPED IN LIPOSOMES

| HA FORMULATION | DOSE/0.5 ml/INOCULUM | | 4 week | | 6 week | | 8 week | | 12 week | |
|---|---|---|---|---|---|---|---|---|---|---|
| | PROTEIN (ug), | LIPID (mg) | EIA | HAI | EIA | HAI | EIA | HAI | EIA | HAI |
| Non-Entrapped | 5.0 | — | 26 | 29 | 516 | 557 | 301 | 368 | 198 | 320 |
| | 0.5 | — | 3 | 9 | 205 | 243 | 126 | 211 | 57 | 106 |
| MLV, CHST, H | 5.0 | 13.6 | 891 | 761 | 7062 | 7241 | 2170 | 3044 | 1581 | 1318 |
| | 0.5 | 1.4 | 52 | 33 | 2655 | 2941 | 1018 | 1237 | 557 | 640 |
| MLV, CHST, L | 5.0 | 1.9 | 147 | 92 | 3886 | 5553 | 3055 | 1810 | 1166 | 1191 |
| | — | — | — | — | — | — | — | — | — | — |
| SPLV, DMPC/C, H | 5.0 | 9.7 | 123 | 80 | 2204 | 1940 | 1548 | 1470 | 776 | 640 |
| | 0.5 | 1.0 | 22 | 23 | 387 | 399 | 233 | 243 | 136 | 121 |
| SPLV, DMPC/C, L | 5.0 | 2.9 | 101 | 89 | 1766 | 1810 | 1042 | 1613 | 767 | 905 |
| | — | — | — | — | — | — | — | — | — | — |

A/Liposomes (MLV, SPLV) were prepared with either 500 mg (H) or 50 mg (L) of lipid (CHST or DMPC/C, 70:30 mole percent)
B/Geometric mean titer (n-51) determined by enzyme-linked immuno assay (EIA) and hemagglutination inhibition (HAI)

We claim:

1. A method of potentiating an immune response in an animal which comprises administering to the animal a dosage form comprising:
   (a) a liposome which comprises:
      (i) a lipid consisting essentially of an organic acid derivative of a sterol; and,
      (ii) an antigenic peptide; and,
   (b) a pharmaceutically acceptable carrier,
wherein said organic acid is selected from the group consisting of a carboxylic, dicarboxylic, polycarboxylic, hydroxy, amino and polyamino acid attached to said sterol at a hydroxyl group by an ether or ester linkage, and wherein the liposome is present in the dosage form in an immunization dose.

2. The method of claim 1, wherein the animal is a human.

3. The method of claim 1, wherein the liposome is a multilamellar liposome.

4. The method of claim 1, wherein the liposome has a size of about 1 micron.

5. The method of claim 1, wherein the sterol is cholesterol.

6. The method of claim 1, wherein the organic acid is a dicarboxylic acid having up to seven carbon atoms.

7. The method of claim 6, wherein the acid is succinic acid.

8. The method of claim 1, wherein the organic acid is citric acid.

9. The dosage form of claim 1, wherein the sterol comprises a salt form of the organic acid.

10. The dosage form of claim 9, wherein the salt form is a tris(hydroxymethyl)aminomethane salt.

11. The method of claim 1, wherein the antigenic peptide is a viral peptide.

12. The method of claim 1, further comprising administering an immunomodulator to the animal.

13. The method of claim 12, wherein the immunomodulator is a cytokine.

14. The method of claim 1, wherein the sterol is cholesterol hemisuccinate.

15. The method of claim 14, wherein the salt form is the tris salt of cholesterol hemisuccinate.

16. The method of claim 14, wherein the immunogen is a viral peptide.

* * * * *